US012161430B2

(12) United States Patent
Wright et al.

(10) Patent No.: US 12,161,430 B2
(45) Date of Patent: Dec. 10, 2024

(54) SURGICAL SUPPORT SYSTEM, DATA PROCESSING APPARATUS AND METHOD

(71) Applicant: Sony Corporation, Tokyo (JP)

(72) Inventors: Christopher Wright, London (GB); Matthew Lawrenson, Lausanne (CH); Naoyuki Hirota, Tokyo (JP)

(73) Assignee: Sony Corporation, Tokyo (JP)

( * ) Notice: Subject to any disclaimer, the term of this patent is extended or adjusted under 35 U.S.C. 154(b) by 907 days.

(21) Appl. No.: 17/261,589

(22) PCT Filed: Sep. 27, 2019

(86) PCT No.: PCT/JP2019/038340
§ 371 (c)(1),
(2) Date: Jan. 20, 2021

(87) PCT Pub. No.: WO2020/075546
PCT Pub. Date: Apr. 16, 2020

(65) Prior Publication Data
US 2021/0259789 A1 Aug. 26, 2021

(30) Foreign Application Priority Data
Oct. 12, 2018 (EP) .................................... 18200263

(51) Int. Cl.
*A61B 34/00* (2016.01)
*A61B 5/16* (2006.01)
(Continued)

(52) U.S. Cl.
CPC ............ *A61B 34/25* (2016.02); *A61B 5/163* (2017.08); *A61B 34/30* (2016.02); *A61B 90/08* (2016.02);
(Continued)

(58) Field of Classification Search
CPC ......... A61B 34/25; A61B 5/163; A61B 34/30; A61B 90/08; A61B 2017/00119;
(Continued)

(56) References Cited

U.S. PATENT DOCUMENTS

| 2014/0126700 A1* | 5/2014 | Gertner | A61F 9/009 378/65 |
| 2014/0160004 A1* | 6/2014 | Katz | A61B 34/25 345/156 |

(Continued)

FOREIGN PATENT DOCUMENTS

| CN | 105078580 A | * 11/2015 | ........... A61B 1/3132 |
| CN | 106659541 A | * 5/2017 | ........... A61B 3/0041 |

(Continued)

OTHER PUBLICATIONS

CN-106659541-A translation (Year: 2017).*
(Continued)

*Primary Examiner* — Kyle T Johnson
(74) *Attorney, Agent, or Firm* — XSENSUS LLP

(57) ABSTRACT

A surgical support system including: an eye behaviour monitoring apparatus that monitors eye behaviour of a surgeon performing a surgical procedure to obtain eye behaviour data of the surgeon; a surgical data generating apparatus that generates surgical data associated with the surgical procedure being performed by the surgeon; a surgical intervention apparatus that performs an intervention procedure for intervening in the surgeon's performance of the surgical procedure; and a data processing apparatus that: determines a value of an intervention parameter associated with the surgical procedure using the obtained eye behaviour data; determines an acceptable range of the value of the intervention parameter using the generated surgical data, and if the determined value of the intervention parameter is outside the determined acceptable range of the value of the
(Continued)

intervention parameter, controls the surgical intervention apparatus to perform the intervention procedure for intervening in the surgeon's performance of the surgical procedure.

20 Claims, 7 Drawing Sheets

(51) Int. Cl.
*A61B 34/30* (2016.01)
*A61B 90/00* (2016.01)
*G06F 3/01* (2006.01)
*A61B 17/00* (2006.01)

(52) U.S. Cl.
CPC .... *G06F 3/013* (2013.01); *A61B 2017/00119* (2013.01); *A61B 2017/00216* (2013.01); *A61B 2034/254* (2016.02); *A61B 2034/258* (2016.02); *A61B 2090/0807* (2016.02)

(58) Field of Classification Search
CPC .... A61B 2017/00216; A61B 2034/254; A61B 2034/258; A61B 2090/0807; A61B 34/35; A61B 2034/2055; A61B 2034/2074; A61B 2034/2046; G06F 3/013
See application file for complete search history.

(56) References Cited

U.S. PATENT DOCUMENTS

| | | | |
|---|---|---|---|
| 2016/0225192 A1* | 8/2016 | Jones | G06F 3/011 |
| 2017/0172675 A1* | 6/2017 | Jarc | A61B 90/361 |
| 2017/0172676 A1* | 6/2017 | Itkowitz | A61B 34/30 |
| 2018/0036884 A1* | 2/2018 | Chen | B25J 9/1676 |
| 2018/0092700 A1* | 4/2018 | Itkowitz | A61B 90/36 |
| 2019/0223968 A1* | 7/2019 | Jarc | A61B 34/35 |
| 2019/0254754 A1* | 8/2019 | Johnson | G06T 19/006 |
| 2020/0401219 A1* | 12/2020 | Freiin von Kapri | A61B 34/25 |
| 2021/0038329 A1* | 2/2021 | Pomati | A61B 90/361 |
| 2021/0259789 A1* | 8/2021 | Wright | A61B 34/30 |
| 2021/0382551 A1* | 12/2021 | Freiin von Kapri | A61B 34/30 |

FOREIGN PATENT DOCUMENTS

| | | | | |
|---|---|---|---|---|
| CN | 107847349 A * | 3/2018 | | A61B 3/0058 |
| EP | 2 742 894 A1 | 6/2014 | | |
| EP | 3622924 A1 * | 3/2020 | | A61B 34/25 |
| JP | 2014113494 A | 6/2014 | | |
| JP | 2017512554 A | 5/2017 | | |
| WO | WO-2019198061 A1 * | 10/2019 | | A61B 17/3403 |
| WO | WO-2022070066 A1 * | 4/2022 | | A61B 1/00009 |

OTHER PUBLICATIONS

EP-3622924-A1 translation (Year: 2020).*
CN-107847349-A translation (Year: 2018).*
CN-105078580-A translation (Year: 2015).*
Suny Downstate Medical Center, "Novice pilots improve visual responses to simulation by watching experts' eye movements", ScienceDaily, Nov. 27, 2017, 2 pages.
Tony Tien,et al.. "Differences in gaze behaviour of expert and junior surgeons performing open inguinal hernia repair", Surg Endosc (2015) 29:405-413, Springer, published online: Aug. 15, 2014, 9 pages.
Tim Stockdale "World's first study of rider's eye movements could reveal the key to show jumping success", The Wayback Machine, http://www.timstockdale.com/worlds-first-study-of-riders-eye-movements-could-reveal-the-key-to-show-jumping-success, printed: Apr. 6, 2021, 3 pages.
International Search Report and Written Opinion mailed on Jan. 8, 2020, received for PCT Application PCT/JP2019/038340, Filed on Sep. 27, 2019, 14 pages.
Tien et al., "Differences in Gaze Behaviour of Expert and Junior Surgeons Performing Open Inguinal Hernia Repair", Surgical Endoscopy, Springer, New York, vol. 29, No. 2, XP035426834, Aug. 15, 2014, pp. 405-413.

* cited by examiner

FIG.2

| Procedure type | Stage | Potential Error Event | Acceptable Error Likelihood | Intervention (non patient critical) | Intervention (patient critical) |
|---|---|---|---|---|---|
| Heart Transplant | Stage 1 | Lung damage | 0.25 | Audible alarm + video feed access suspended | Audible alarm |
| Heart Transplant | Stage 1 | Artery damage | 0.25 | Audible alarm + haptic alarm + video feed access suspended | Audible alarm + haptic alarm |
| Heart Transplant | Stage 2 | Organ / Muscle group damage | 0.35 | AR error visualisation | AR error visualisation |
| Heart Transplant | Stage 2 | Transplanted heart damage | 0.20 | AR error visualisation + audible alarm + robot operation suspended | AR error visualisation + audible alarm + robot operation suspended |
| Heart Transplant | Stage 3 | Subsurface blood vessel damage | 0.25 | Automatic robot operation correction. Optional AR error visualisation + haptic alarm. | AR error visualisation + haptic alarm. |

SURGICAL SUPPORT SYSTEM, DATA PROCESSING APPARATUS AND METHOD

CROSS-REFERENCE TO RELATED APPLICATIONS

The present application is based on PCT filing PCT/JP2019/038340, filed Sep. 27, 2019, which claims priority to EP 18200263.4, filed Oct. 12, 2018, the entire contents of each are incorporated herein by reference.

TECHNICAL FIELD

The present disclosure relates to a surgical support system, data processing apparatus and method.

BACKGROUND

The "background" description provided herein is for the purpose of generally presenting the context of the disclosure. Work of the presently named inventors, to the extent it is described in the background section, as well as aspects of the description which may not otherwise qualify as prior art at the time of filing, are neither expressly or impliedly admitted as prior art against the present disclosure.

Serious surgical errors are referred to as "never events", as they are often avoidable and therefore should not happen. Never events include leaving a surgical tool inside the patient and operating on the wrong patient. Less serious (but still dangerous and costly) mistakes, such as the accidental severing of a blood vessel, are referred to as technical errors. Despite processes such as surgical timeouts and checklists being put in place to prevent them, surgical errors continue to occur in medical facilities globally. For example, serious cases in the UK were found to have increased in recent years and research suggests that medical error is the third leading cause of death in the United States.

Surgical errors can range from wrong site surgery or an incorrect procedure to a small slip of the hand at a critical point, and each can pose significant risk to the patient. Errors commonly arise due to a lack of information, which can increase the surgeon's level of uncertainty when making decisions. This can result from, for example, poor surgical team or healthcare provider communication or missing data. Surgical specialisms can also experience their own unique issues, making error classification more complex.

Human factors are also a major (and unpredictable) cause of surgical errors-poor decision-making, selecting the wrong technique for a particular action, and simply executing an action incorrectly can have serious implications for the patient and hospital. Furthermore, surgeons may avoid admissions of guilt or of not having enough knowledge during a procedure in order to escape workplace reprimands or legal reprisals, an issue which could be avoided if comprehensive checks existed to prevent these errors from occurring in the first instance.

Future operating rooms are likely to see increasing collaboration between operation robots and human surgeons, which could offer an avenue to reducing the number of avoidable surgical errors that occur. Such systems may enable an adaptable task responsibility relationship, whereby the roles of the robot and human may vary with the status of the operation, and the robot may be able to act as an additional safety net in the prevention of surgical mistakes.

A problem remains, however, in how to successfully implement the collaboration between operation robots and human surgeons and, more generally, in how to further reduce the number of avoidable surgical errors that occur.

SUMMARY

The present disclosure is defined by the claims.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF DRAWINGS

A more complete appreciation of the disclosure and many of the attendant advantages thereof will be readily obtained as the same becomes better understood by reference to the following detailed description when considered in connection with the accompanying drawings, wherein:

FIG. 2 schematically shows example information used by the surgical support system in determining a suitable surgical intervention procedure, according to an embodiment;

DESCRIPTION OF EMBODIMENTS

Figure 1:
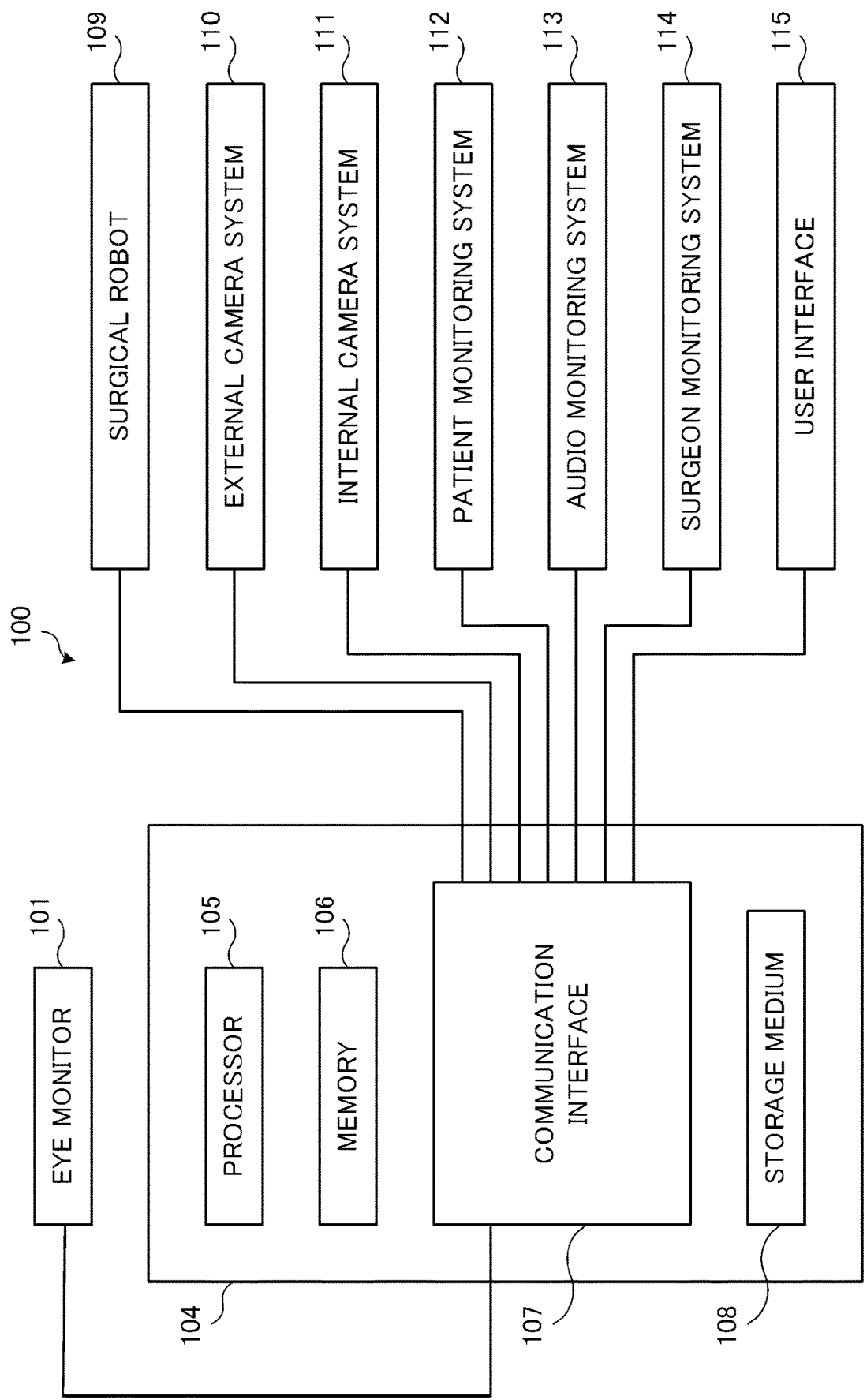
FIG. 1 schematically shows a surgical support system, according to an embodiment.

Referring now to the drawings, wherein like reference numerals designate identical or corresponding parts throughout the several views.

The present technique uses eye behaviour monitoring technology to collect eye behaviour data to help assess the performance of a human surgeon and to make an intervention during a surgical procedure in the case that the eye behaviour data indicates that the occurrence of a surgical error is likely.

Eye behaviour monitoring technologies are relatively well-established and have been implemented in various existing technologies for the purpose of augmented reality (AR) and virtual reality (VR) platforms. An advantage enabled by the development of eye behaviour monitoring technology is the ability to identify what an individual is visually interested in. While this ability is currently most widely applied in AR and VR headsets, it also has applications in advertising, market research and medical accessibility.

At their most basic level, eye movements indicate what a person is looking at. However, eye movements can also be used to obtain information about a person's ability to perform in a certain situation. Research has shown that expert and junior doctors exhibit differences in their gaze patterns (that is, the pattern of movement of the location in space at which the doctor is looking) during surgery that can be attributed to the individual's level of skill (NPL 1). Similarly, the tiny eye movements of elite horse riders which are made while planning a jump can indicate their likely success (NPL 2). The visual strategies of experienced riders differed to those of less competent riders in the amount of time the rider spent visually fixated on a particular stage of the jump and how early the fixation began.

Studies have also shown that novice performers can learn from the eye movements of more skilled individuals. The visual responses of novice military pilots to a simulated emergency procedure were found to improve after observing the eye movements of expert pilots (NPL 3). In this case, the difference between novice and skilled pilots was so pronounced that an algorithm was able to classify the two in more than 80% of cases.

In particular, aspects of eye behaviour which may anticipate mistakes include:
1. Short dwell times (time spent looking at an area of interest).
2. Lower fixation frequency (number of times gaze was focused on an area of interest in a time period).
3. Velocity and distance of saccades. Saccades are rapid movements of the eyes that abruptly change the point of fixation. Saccades can be used to identify expert and novice drivers. In particular, experts have smaller saccade velocity and distance than novices because they are able to utilise peripheral vision more effectively than novices. Saccade velocity is the speed with which the eyes move when the point of fixation changes during a saccade. Saccade distance is the distance by which the eyes move when the point of fixation changes during a saccade.
4. Oversight of an important visual feature.
5. Mismatch between pupil dilation (which reflects mental effort) and estimated task difficulty. Pupil dilation increases with increased cognitive load and decreases with reduced cognitive load. A lack of pupil dilation during a difficult task may indicate a lack of concentration or cognitive involvement.

Embodiments of the present technique use eye behaviour monitoring technology to help reduce the occurrence of surgical errors. This is done by addressing one or more of the following points:
1. How to pre-empt and prevent a surgical mistake without causing undue distraction to the surgeon while they operate.
2. How to determine how a surgeon's uncertainty may affect a patient, and allow for some level of uncertainty in scenarios that require it (i.e. to prevent harm to the patient through inaction).
3. How to select an appropriate response to a predicted surgical error, based on the potential severity and risk to the patient.
4. How to reduce the chance of mistakes occurring during high pressure, critical scenarios where it is necessary for the surgeon to work quickly.
5. How to accurately identify the cause of a surgeon's uncertainty within their field-of-view and enable tailored uncertainty responses.

FIG. 1 shows a surgical support system 100 according to an embodiment. The surgical support system 100 comprises an eye behaviour monitoring apparatus (eye monitor) 101, one or more surgical data generating apparatuses (e.g. one or more of apparatuses 109 to 115), one or more surgical intervention apparatuses (e.g. one or more of apparatuses 109 to 115) and a data processing apparatus 104.

The eye behaviour monitoring apparatus 101 is operable to perform eye behaviour monitoring of a surgeon performing a surgical procedure to obtain eye behaviour data of the surgeon. In an embodiment, the eye behaviour monitoring apparatus uses any suitable eye tracking technique known in the art to obtain eye tracking data. The eye tracking data includes data indicative of the gaze of the surgeon (that is, the point in space at which the surgeon is looking). This gaze is determined by the eye behaviour monitoring apparatus based on the position of the surgeon's pupils relative to the surgeon's head and/or the position of the surgeon's head, for example. In an embodiment, the eye behaviour monitoring apparatus uses any suitable pupil monitoring technique to obtain pupil monitoring data indicative of behaviour of a pupil of each of one or more of the surgeon's eyes (for example, the pupil dilation of the surgeon or saccade velocity and/or distance).

The eye behaviour monitoring apparatus 101 thus carries out both eye tracking and pupil monitoring in order to monitor the behaviour of the surgeon's eyes. The eye tracking comprises tracking the gaze of the surgeon (e.g. based on a live captured video image of the surgeon's eyes) to determine eye tracking data (for example, the dwell time on a region of interest, the fixation frequency on a region of interest and/or whether or not a region of interest has been overlooked). The resulting eye tracking data may be associated with information about the region of interest. The pupil monitoring comprises monitoring the surgeon's pupils (e.g. based on a live captured video image of the surgeon's eyes) to determine pupil monitoring data (for example, the pupil dilation of the surgeon and/or the saccade velocity and/or distance). The eye tracking data and pupil monitoring data are examples of eye behaviour data.

Information may be derived from the eye behaviour data by the data processing apparatus 104 to indicate an increased likelihood of the surgeon making an error during the surgical procedure.

In one example, the likelihood of an error occurring is deemed to increase if the surgeon has an acceptably short dwell time on an area of interest. A dwell time is unacceptably short if it is less than a predetermined dwell time threshold, for example (the predetermined dwell time threshold being determined depending on the procedure and/or stage of the procedure taking place, for example). In an example, the dwell time is the average time that the surgeon spends looking at the region of interest during the surgical procedure (or during a certain stage of the surgical procedure).

In another example, the likelihood of an error occurring is deemed to increase if the surgeon has an unacceptably low fixation frequency on an area of interest. A fixation frequency is unacceptably low if it is less than a predetermined fixation frequency threshold, for example (the predetermined fixation frequency threshold being determined depending on the procedure and/or stage of the procedure taking place, for example).

In another example, the likelihood of an error occurring is deemed to increase with higher saccade velocity and/or distance. A saccade velocity and/or distance is unacceptably high if it is greater than a predetermined saccade velocity and/or distance threshold, for example (the predetermined saccade velocity and/or distance threshold being determined depending on the procedure and/or stage of the procedure taking place, for example).

In another example, the likelihood of an error occurring is deemed to increase following oversight by the surgeon of an important visual feature. Oversight of a visual feature occurs when the surgeon's gaze does not fall on that visual feature (indicating that the surgeon has not noticed it).

In another example, the likelihood of an error occurring is deemed to increase if there is a mismatch between pupil dilation (which reflects mental effort) and estimated task difficulty. A pupil dilation is unacceptably large if it is greater than a predetermined pupil dilation threshold, for example (the predetermined pupil dilation threshold being determined depending on the procedure and/or stage of the procedure taking place, for example). In order to take into account the fact that different surgeons may have different respective ranges of pupil size, the pupil dilation and predetermined pupil dilation threshold may be determined as a percentage of a reference pupil dilation. For example, if the pupil diameter doubles in size compared to that of the reference pupil dilation, then the pupil dilation is determined to be +50% (positive 50%). If the pupil diameter halves in size compared to that of the reference pupil dilation, then the pupil dilation is determined to be −50% (negative 50%). The reference pupil dilation is determined during a calibration procedure (e.g. by getting the surgeon to look at a camera (not shown) of the eye behaviour monitoring apparatus 101 under predetermined lighting conditions and measuring the pupil dilation to obtain the reference pupil dilation) which takes place prior to the surgery.

The data processing apparatus 104 comprises a processor 105, memory 106, communication interface 107 and storage medium 108. The communication interface 107 is for the input and output of electronic information to and from the data processing apparatus 104. For example, the eye behaviour data from the eye behaviour monitoring apparatus 101 and surgical data from the one or more surgical data generating apparatuses are received by the communication interface 107 as input information. Also, an intervention signal for controlling the one or more surgical intervention apparatuses to perform an intervention procedure is transmitted to the one or more surgical intervention apparatuses by the communication interface 107 as output information. The communication interface 107 also allows data to be exchanged between any two apparatuses connected to the communication interface 107. The processor 105 enables the data processing apparatus 104 to carry out its operations by processing suitable electronic instructions. The memory 106 is for storing electronic instructions to be processed by processor 105 and for storing input and output data associated with the electronic instructions. The storage medium 108 (e.g. in the form of a hard disk drive, solid state drive, tape drive or the like) is for long term storage of data. Each of the processor 105, memory 106, communication interface 107 and storage medium 108 are implemented using appropriate circuitry, for example.

The communication interface 107 is operable to receive surgical data associated with the surgical procedure being performed by the surgeon. The surgical data is received from the one or more surgical data generating apparatuses during the surgical procedure. In the example of FIG. 1, there is a plurality of surgical data generating apparatuses which each provide surgical data to the communication interface 107.

One example surgical data generating apparatus is a surgical robot 109. The surgical robot 109 is a robotic system which assists the surgeon in performing surgery. Various surgical robots are known in the art and surgery involving surgical robots is known as robot-assisted surgery. The surgical data provided to the communication interface 107 by the surgical robot 109 comprises, for example, values of one or more parameters associated with one or more functions of the robot carried out by the robot during the surgical procedure (e.g. the speed of a cutting blade used by the robot or the depth inside the patient of a robotic arm of the robot). The one or more parameters are monitored by appropriate circuitry of the robot, for example.

Another example surgical data generating apparatus is an external camera system 110. This comprises one or more cameras (not shown) which capture images of the operating room within which the surgery takes place. The captured images include, for example, the surgeon, the patient, other members of the surgical team and other surgical apparatuses in the room. The surgical data provided to the communication interface 107 by the external camera system 110 comprises the captured images.

Another example of a surgical data generating apparatus is an internal camera system 111. This comprises one or more cameras (not shown, e.g. one or more endoscopic cameras, as known in the art) which capture images inside the patient's body. The captured images may also include, for example, the surgeon's hands and any surgical apparatuses which enter the part of the patient's body captured by the internal camera system during the surgery (e.g. cutting tools held by the surgeon or an end of an arm of the surgical robot 109). The surgical data provided to the communication interface 107 by the internal camera system 111 comprises the captured images.

Another example of a surgical data generating apparatus is a patient monitoring system 112. The patient monitoring system monitors one or more physiological parameters of the patient during the surgery and generates data indicative of a value of each of these physiological parameters. This allows the status of the patient to be monitored during the surgery. An example of a patient monitoring system is an electrocardiograph (ECG) which generates ECG data. The surgical data provided to the communication interface 107 by the patient monitoring system 112 comprises the data indicative of the value of each of the monitored physiological parameters of the patient.

Another example of a surgical data generating apparatus is an audio monitoring system 113. This comprises one or more microphones (not shown) which capture sound in the operating room within which the surgery takes place. The captured sounds include, for example, speech uttered by the surgeon or other members of the surgical team and audible signals (e.g. alarms) emitted by other surgical apparatuses. The surgical data provided to the communication interface 107 by the audio monitoring system 113 comprises data indicative of the captured sounds. The data processing apparatus 104 is configured to analyse the captured sounds in order to determine what the captured sounds are. It does this, for example, by performing a frequency analysis of a captured sound and comparing the resulting frequency spectrum with the frequency spectrum of known sounds stored in the storage medium 108 (suitable techniques for this are known in the art). This allows the data processing apparatus 104 to, for example, recognise speech of the surgeon (allowing the surgeon to provide surgical data to the system vocally) or to recognise the meaning of specific audible signals emitted by other surgical apparatuses.

Another example of a surgical data generating apparatus is a surgeon monitoring system 112. The surgeon monitoring system monitors one or more physiological parameters of the surgeon during the surgery and generates data indicative of a value of each of these physiological parameters. The surgeon monitoring system comprises, for example, a heart rate monitor to monitor the heart rate of the surgeon and/or a sweat monitor to monitor how much a surgeon is sweating (perspiring). This helps allow the stress levels of the surgeon to be monitored. For example, when the surgeon is more stressed, their heart rate tends to increase and they tend to sweat more and when the surgeon is less stressed, their heart rate tends to decrease and they tend to sweat less. The surgical data provided to the communication interface 107 by the surgeon monitoring system 114 comprises the data indicative of the value of each of the monitored physiological parameters of the surgeon.

Another example of a surgical data generating apparatus is a user interface 115. The user interface allows a user (e.g. the surgeon or another member of the surgical team) to manually enter surgical data to be provided to the communication interface 107. It also allows data output by the communication interface 107 (e.g. an alert signal) to be provided to the user in an understandable format. In one example, the user interface 115 comprises a touch screen or the combination of a head mountable display (HMD) and input device (e.g. handheld controller or voice recognition device). The user interface 115 may also comprise a haptic feedback device (e.g. electrical vibrator) and/or audio loudspeaker. In one example, the surgical data entered by the user is data indicative of the type of surgical procedure to take place. Prior to the start of the surgical procedure, the selects the surgical procedure type using, for example, an appropriate graphical user interface (GUI) menu system displayed on the touch screen or HMD. In another example, data output by the communication interface 107 comprises an alert signal. In response to receiving the alert signal, the touch screen or HMD outputs a visual alert, the loudspeaker (if present) outputs an audible alert and the haptic feedback device (if present) outputs a haptic alert. The user is thus alerted by the visual, audible and/or haptic alert.

The communication interface 107 is also operable to output an intervention signal to the one or more surgical intervention apparatuses in the case that analysis of the eye behaviour data of the surgeon indicates that an intervention needs to be made in order to alleviate the risk of a surgical error. The one or more surgical intervention apparatuses perform an intervention procedure in response to receiving the intervention signal.

In one example, the intervention signal is an alert signal and the intervention procedure comprises outputting an alert to the user. For example, the alert signal may cause the user interface 115 to output an audible, visual and/or haptic alert (as previously described). In the case of an alert, no action is taken to interrupt the surgery (that is, the surgeon is not prevented from continuing the surgical procedure and it is therefore the decision of the surgeon as to whether or not the surgical procedure continues). In this case, the user interface 115 is the surgical intervention apparatus. Furthermore, this alert signal may be varied depending on how much the error likelihood exceeds the acceptable error likelihood. For example, in the case of the error likelihood far exceeding the acceptable error likelihood (i.e. by more than a predetermined threshold), output audio (e.g. beep or alarm sound) of the alert signal may be louder (i.e. above a predetermined volume threshold). In another example, in case of the alert signal comprising a visual alert (e.g. a visible marker or notification indicating the error likelihood displayed on the user interface 115), the visual representation may be varied. For example, the visual representation may be displayed on more displays, displayed over a larger portion of the display or displayed at a more central position on the display. Depending on the comparison of the error likelihood and acceptable error likelihood, the system may change the alert signal from only one of an audible, visual or haptic alert to combination of more than one of them.

In another example, the intervention signal is an adjustment signal and the intervention procedure comprises adjusting an operation of a surgical apparatus used by the surgeon to carry out the surgical procedure so as to pre-empt the error in the surgical procedure. In the case of an adjustment, action is taken to interrupt the surgery in order to pre-empt the error (that is, the surgeon is prevented from continuing the surgical procedure and therefore the decision as to whether or not the surgical procedure continues is not taken by the surgeon). In this case, the surgical apparatus whose operation is adjusted is the surgical intervention apparatus.

In the example of FIG. 1, the surgical robot 109 and user interface 115 are examples of surgical intervention apparatus which are able to adjust their operation in response to receiving an adjustment signal from the communication interface 107.

An example of an adjustment carried out by the surgical robot 109 is when the surgeon is controlling an arm of the robot to make a surgical incision in the patient. The robot receives the adjustment signal and, in response, temporarily suspends functionality the arm.

An example of an adjustment carried out by the user interface 115 is when the surgeon is viewing their actions on the patient's body during the surgical procedure via a video feed (captured by an endoscopic camera or the like of the internal camera system 111) displayed using the user interface 115. The user interface receives the adjustment signal and, in response, temporarily suspends display of the video feed.

In both these examples, the surgeon is temporarily (that is, for a predetermined finite period of time, e.g. 30 seconds) prevented from continuing the surgical procedure in order to alleviate the risk of an error being made. This allows the surgeon to, for example, take a mental break and, if necessary, plan adjustments to their technique or to consult with a colleague so as to reduce the likelihood of them making the error (thereby allowing the procedure to proceed safely).

Each surgical data generating apparatus which provides surgical data to the communication interface 107 does so via a suitable wired and/or wireless connection (as known in the art). The wired and/or wireless connection may be part of a computer network such as the internet. Each surgical intervention apparatus which receives an intervention signal from the communication interface 107 does so via a suitable wired or wireless connection (as is known in the art). The wired and/or wireless connection may be part of a computer network such as the internet.

In an embodiment, the data processing apparatus 104 determines the likelihood of the surgeon making an error in the surgical procedure using the eye behaviour data. The eye behaviour data is obtained by the eye behaviour monitoring apparatus 101 and transmitted to the communication interface 107 via a suitable wired or wireless connection (as is known in the art). The wired and/or wireless connection may be part of a computer network such as the internet. The data processing apparatus 104 determines an acceptable likelihood of the surgeon making an error in the surgical procedure using the surgical data. If the determined likelihood of the surgeon making an error in the surgical procedure (this will be referred to as the determined error likelihood) exceeds the acceptable likelihood of the surgeon making an error in the surgical procedure (this will be referred to as the acceptable error likelihood), then the data processing apparatus 104 controls the one or more surgical intervention apparatuses to perform an appropriate intervention procedure by sending an appropriate intervention signal (e.g. an alert signal and/or adjustment signal).

In embodiments, by using eye behaviour monitoring of the surgeon to determine the likelihood of the surgeon making an error and to thus determine an appropriate intervention procedure, it becomes easier to predict and alleviate the occurrence of errors. At the same time, since the surgeon does not have to perform any additional actions during the surgical procedure in order for the eye behaviour monitoring to take place, unnecessary disruption of the surgeon's workflow is alleviated.

In an embodiment, the surgical data is indicative of at least one of a type of the surgical procedure taking place and a current stage of the surgical procedure. The data processing apparatus 104 determines the acceptable likelihood of the surgeon making an error in the surgical procedure using the surgical data.

The type of surgical procedure identifies which surgical procedure is performed by the surgeon. For example, the surgical procedure type may be a heart transplant, coronary artery bypass grafting or a knee replacement. The current stage of the surgical procedure is one of a plurality of stages of the surgical procedure. Each stage is a subprocedure of the surgical procedure. The stages of the surgical procedure must each be completed successfully in an appropriate order to allow the surgical procedure to be completed successfully. The necessary stages (and their order) will generally vary for different surgical procedure types. Examples of stages include making an incision on a certain organ of the patient, moving or removing a part of an organ of the patient and suturing an incision on a certain organ of the patient.

In an embodiment, each surgical procedure type and/or one or more of the stages the surgical procedure type is associated with one or more corresponding potential error events. A potential error event is an event (e.g. accidental damage to a healthy organ of the patient) which will potentially occur during the current stage if the surgeon makes an error. Each potential error event is associated with a corresponding acceptable error likelihood of that potential error event occurring. During the surgical procedure, the determined error likelihood of each relevant potential error event at a given time is determined using the eye behaviour data of the surgeon. If the determined error likelihood of a potential error event exceeds the acceptable error likelihood for that potential error event, then a suitable intervention procedure is made.

A potential error event may be associated with the surgical procedure in general. In this case, the determined error likelihood is continually updated, base on the surgeon's eye behaviour data, for the entire duration of the surgical procedure. Alternatively, a potential error event may be associated with a particular stage of the surgical procedure. In this case, the determined error likelihood is continually updated, based on the surgeon's eye behaviour data, for only the duration of that particular stage.

In an embodiment, information indicative of the surgical procedure type is entered by a user prior to beginning the surgical procedure via the user interface 115. This information is provided as surgical data to the data processing apparatus 104. The data processing apparatus 104 looks up the indicated surgical procedure type in a database stored in the storage medium 108. The database identifies each stage of the indicated surgical procedure type, each potential error event associated with the indicated surgical procedure type (and the stage of the surgical procedure type with which that potential error event is associated, if applicable) and the acceptable error likelihood associated with each identified potential error event.

An example of information stored in the database is shown in FIG. 2.

The surgical procedure type in FIG. 2 is a heart transplant. The heart transplant is shown to have three stages ("Stage 1", "Stage 2" and "Stage 3"), each of which is associated with one or more potential error events. Each potential error event, in turn, is associated with an acceptable error likelihood and one or more intervention procedures. It will be appreciated that, for case of explanation, this is a simplified example. In reality, a surgical procedure such as a heart transplant may have many more stages and each stage may have many more associated potential error events.

Although not shown in FIG. 2, it is possible that a potential error event is associated with the heart transplant as a surgical procedure in general (rather than with only a particular stage of the heart transplant). In this case, the potential error event and its associated acceptable error likelihood and one or more intervention procedures is identified in the database but is not associated with a specific stage of the heart transplant. In this case, the "Stage" column may read "All", for example (indicating that the potential error event and its associated acceptable error likelihood and one or more intervention procedures is applicable to all stages of the heart transplant).

A potential error event may also be of a generic type. A generic potential error event is a potential error event not specific to a certain type of error which may occur (e.g. on a certain part of the patient's body) but which has an acceptable likelihood which is exceeded in the case that the risk of the surgeon making an error increases in general. For example, if the surgeon suddenly has a very wide pupil dilation (indicating a severe inability to concentrate, brought on by a sudden illness or fatigue, for example), then the likelihood of an error occurring in general may be determined to be unacceptably high, even if the exact nature of the potential error cannot be determined. The monitored eye behaviour parameters associated with a generic potential error event are eye behaviour parameters indicative of the general level of concentration, fatigue, etc. of the surgeon, for example. The intervention procedure(s) associated with a generic potential error event indicate that the potential error event is generic (e.g. by displaying a suitable visual alert using the user interface 115 or sounding a particular audible alarm) but do not indicate a particular part of the patient's body. A generic potential error event is treated in the same way as any other potential error event in terms of the way it is stored and retrieved by the data processing apparatus 108 (e.g. as exemplified in the table of FIG. 2).

The one or more intervention procedures associated with each potential error event are divided into two categories. The first category is a non-patient critical category. This defines one or more intervention procedures to be applied in the case that the determined error likelihood exceeds the acceptable error likelihood for the potential error event concerned when the patient is in a non-critical condition. The patient is in a non-critical condition when a value of each of one or more relevant physiological parameters of the patient (as indicated by the surgical data received from the patient monitoring system 112) is within a normal range. The relevant one or more physiological parameters and their respective normal ranges are determined for a given surgical procedure type in advance (e.g. based on accepted knowledge of the medical community) and are stored in the storage medium 108, for example. The second category is a patient critical category. This defines one or more intervention procedures to be applied in the case that the determined error likelihood exceeds the acceptable error likelihood for the potential error event concerned when the patient is in a critical condition. The patient is in a critical condition when a value of each of the one or more relevant physiological parameters of the patient is outside the normal range. In one example, the relevant physiological parameters are indicative of the status of one or more of the patient's vital signs.

Determining the intervention procedure depending on whether or not the patient is in a critical or non-critical condition helps to apply intervention procedures safely. For example, when the patient is in a non-critical condition, the safest intervention procedure may involve an adjustment in which the surgeon is temporarily prevented from continuing the surgical procedure. Because the patient is non-critical, it is determined to be safer to temporarily suspend the procedure (thereby delaying completion of the procedure) so as to alleviate the risk of the surgeon making an error. On the other hand, when the patient is in a critical condition, the safest intervention procedure may involve an alert only (that is, no adjustment). The surgeon is thus not prevented from continuing the surgical procedure. Because the patient is critical, it is determined to be safer to allow the surgeon to continue with the procedure (despite the risk of the surgeon making an error) than to delay completion of the procedure.

It will be appreciated that, even though only two categories of intervention procedure are shown, there may be any number of categories, each associated with a respective set of ranges of values of one or more physiological parameters of the patient. The intervention procedure(s) of a particular category are then applied (when the determined error likelihood exceeds the acceptable error likelihood) when the measured values of the one or more physiological parameters of the patient are within the set of ranges associated with that category. This allows the most appropriate intervention procedure to be applied depending on the physical status of the patient, thereby helping to improve patient safety.

In the example of FIG. 2, Stage 1 of the heart transplant involves the surgeon making an incision in the flesh between a lung and an artery of the patient. Stage 1 is associated with two potential error events. The first one is damage to the lung (with an acceptable error likelihood of 0.25) and the second one is damage to the artery (with an acceptable error likelihood of 0.25).

For the first potential error event (lung damage), an intervention procedure will be implemented if the determined error likelihood of the surgeon (based on the surgeon's eye behaviour data) exceeds 0.25. If the patient is in a non-critical condition (and therefore avoiding a potential surgical error is more important than avoiding a delay of completion of Stage 1), then the intervention procedure comprises the communication interface 107 outputting an alert signal to initiate an audible alarm (to alert the surgeon of the unacceptably high likelihood that they will make an error) and, furthermore, outputting an adjustment signal to initiate temporary suspension of display of a video feed being used by the surgeon to view the area in which the incision is to be made (thus preventing the surgeon from continuing with the incision). On the other hand, if the patient is in a critical condition (and therefore avoiding a delay of completion of Stage 1 is more important than avoiding a potential surgical error), then the intervention procedure comprises the communication interface 107 outputting the alert signal only (thus initiating the audible alarm to alert the surgeon of the unacceptably high likelihood that they will make an error but not preventing the surgeon from continuing with the incision by suspending display of the video feed).

For the second potential error event (artery damage), an intervention procedure will also be implemented if the determined error likelihood of the surgeon (based on the surgeon's eye behaviour data) exceeds 0.25. If the patient is in a non-critical condition (and therefore avoiding a potential surgical error is more important than avoiding a delay of completion of Stage 1), then the intervention procedure comprises the communication interface 107 outputting an alert signal to initiate an audible alarm and a haptic alarm (to alert the surgeon of the unacceptably high likelihood that they will make an error) and, furthermore, outputting an adjustment signal to initiate temporary suspension of display of the video feed being used by the surgeon to view the area in which the incision is to be made (thus preventing the surgeon from continuing with the incision). On the other hand, if the patient is in a critical condition (and therefore avoiding a delay of completion of Stage 1 is more important than avoiding a potential surgical error), then the intervention procedure comprises the communication interface 107 outputting the alert signal only (thus initiating the audible alarm and haptic alarm to alert the surgeon of the unacceptably high likelihood that they will make an error but not preventing the surgeon from continuing with the incision by suspending display of the video feed).

In this case, the second potential error event (artery damage) is associated with an audible alarm and a haptic alarm whereas the first potential error event (lung damage) is associated with an audible alarm only. This helps the surgeon to identify the potential error event more quickly and may also be used to reflect the relative seriousness of the potential error event. For example, a more serious potential error event (e.g. artery damage in this case) may be associated with a greater number of simultaneously initiated alarm types (both audible and haptic alarms in this case) whereas a less serious potential error event (e.g. lung damage in this case) may be associated with a smaller number of simultaneously initiated alarm types (an audible alarm only in this case).

In the example of FIG. 2, Stage 2 of the heart transplant involves the surgeon attaching a blood vessel to the transplanted heart. Stage 2 is associated with two potential error events. The first one is damage to the surrounding organs or muscle groups (with an acceptable error likelihood of 0.35) and the second one is damage to the transplanted heart itself (with an acceptable error likelihood of 0.20).

For the first potential error event (surrounding organ or muscle group damage), an intervention procedure will be implemented if the determined error likelihood of the surgeon (based on the surgeon's eye behaviour data) exceeds 0.35. For this potential error event, even though it is undesirable, it is not a sufficiently serious potential error event for the surgery to be suspended (even if the patient is in a non-critical condition). Thus, in this case, the intervention procedure for both the patient being in a non-critical condition and the patient being in a critical condition is the same. Namely, the intervention procedure comprises the communication interface 107 outputting an alert signal to initiate superimposing an augmented reality (AR) visualisation over a surgical image of the portion of the surrounding organ or muscle group (displayed using the user interface 115) which is susceptible to damage (this being a region of interest in this case). However, no adjustment signal is output by the communication interface 107, and thus the surgeon is not prevented from continuing with the procedure (that is, the decision as to whether to continue with the procedure or to take a break is left to the surgeon). The portion of the surrounding organ or muscle group indicated by the superimposed AR visualisation may be detected based on the surgeon's eye behaviour data. In one example, it is a portion for which the surgeon has a dwell time and/or fixation frequency which is below a predetermined dwell time and/or fixation frequency value. The AR image visualisation both alerts the surgeon of the unacceptably high likelihood that they will make an error and informs them of the nature of the potential error (i.e. damage to the identified portion of the surrounding organ or muscle group).

For the second potential error event (transplanted heart damage), an intervention procedure will be implemented if the determined error likelihood of the surgeon (based on the surgeon's eye behaviour data) exceeds 0.20. For this potential error event, it is a sufficiently serious potential error event that the surgery should be suspended (even if the patient is in a critical condition). Thus, in this case, the intervention procedure for both the patient being in a non-critical condition and the patient being in a critical condition is the same. Namely, the intervention procedure comprises the communication interface 107 outputting an alert signal to initiate superimposing an augmented reality (AR) visualisation over an image of the portion of the transplanted heart (displayed using the user interface 115) which is susceptible to damage (this being a region of interest in this case) and to initiate an audible alarm. Furthermore, the intervention procedure comprises the communication interface 107 outputting an adjustment signal to suspend operation of a surgical robot (e.g. surgical robot 109) currently being used by the surgeon to carry out the procedure (thus temporarily preventing the surgeon from proceeding with the procedure). Again, the portion of the transplanted heart indicated by the superimposed AR visualisation may be detected based on the surgeon's eye behaviour data. In one example, it is a portion for which the surgeon has a dwell time and/or fixation frequency which is below a predetermined dwell time and/or fixation frequency value. The AR image visualisation both alerts the surgeon of the unacceptably high likelihood that they will make an error and informs them of the nature of the potential error (i.e. damage to the identified portion of the transplanted heart).

In the example of FIG. 2, Stage 3 of the heart transplant involves the surgeon making a further, small and precise incision using the surgical robot 109. The surgeon controls the robot to make the incision using the user interface 115 (control signals being transmitted from the user interface 115 to the surgical robot 109 via the data processing apparatus 104), for example. As the incision is being made, the predicted path of the incision is determined based on the eye behaviour data of the surgeon. For example, the predicted path may be determined to be a straight line defined between the current positon of the cutting tool (e.g. scalpel) being used to make the incision and the current gaze position of the surgeon. The predicted path of the incision is shown superimposed on a displayed image of the portion of the patient's body along which the incision is to be made. Stage 3 is associated with only one potential error event. This is damage to a sub-surface blood vessel located in the path of the incision. Such a situation may occur if the surgeon (e.g. due to a lapse of concentration) does not notice when the sub-surface blood vessel is located along the predicted path of the incision. The acceptable error likelihood of the potential error event is 0.25. An intervention procedure will therefore be implemented for the potential error event of Stage 3 if the determined error likelihood of the surgeon (based on the surgeon's eye behaviour data) exceeds 0.25. The determined error likelihood may be determined based on the distance between the cutting tool being used to make the incision and any sub-surface blood vessel located along the predicted incision path (with a greater distance being associated with a lower determined error likelihood and a lesser distance being associated with a higher determined error likelihood).

If the patient is in a non-critical condition, then the intervention procedure comprises the communication interface 107 outputting an adjustment signal to control the robot to override the control instructions from the surgeon and to control the cutting tool deviate from the predicted incision path so as to avoid the sub-surface blood vessel. The override is temporary so that control is returned to the surgeon after the potential error event has been avoided. The surgeon thus remains in control of the robot (keeping the surgeon in control of the procedure and thereby allowing the patient to benefit from the surgeon's human experience and ability to quickly interpret a wide range of types of information) except in the case where the likelihood of the surgeon causing the potential error event becomes unacceptably high (in which case, the robot temporarily overrides the surgeon's control in order to avoid the error). The intervention procedure may also comprise the communication interface 107 outputting an alert signal to initiate a haptic alarm and to initiate superimposing of an augmented reality (AR) visualisation over an image of the sub-surface blood vessel (displayed using the user interface 115) which may be damaged (this being a region of interest in this case). The outputting of such an alert signal is optional in this case. For example, whether or not the alert signal is output may depend on preconfigured preferences of the surgeon or may depend on the extent to which the robot must override the surgeon's control. In the latter case, for example, if the robot must override the surgeon's control for a time less than a predetermined threshold time (implying a relatively small potential deviation from the predicted incision path), then the alert signal is not output (since the potential deviation is only small, it is more beneficial for the surgeon not to be distracted by the AR visualisation and haptic alarm than to be informed of the increased likelihood of them making an error). On the other hand, if the robot must override the surgeon's control for a time greater than the predetermined threshold time (implying a relatively large potential deviation from the predicted incision path), then the alert signal is output (since the potential deviation is large, it is more beneficial for the surgeon to be informed of the increased likelihood of them making an error than to not be distracted by the AR visualisation and haptic alarm).

If the patient is in a critical condition, then the intervention procedure does not comprise the communication interface 107 outputting an adjustment signal to control the robot to override the control instructions from the surgeon. This allows the surgeon to remain in control of the robot at all times whilst the patient is in a critical condition (when the surgeon's human experience and ability to interpret a wide range of types of information is most beneficial). The intervention procedure does, however, comprise the communication interface 107 outputting the alert signal to initiate the haptic alarm and to initiate superimposing of the augmented reality (AR) visualisation over the image of the sub-surface blood vessel (displayed using the user interface 115) which may be damaged (this being a region of interest in this case). In the case of the patient being in a critical condition, the alert signal is always output by the communication interface 107 so as to allow the surgeon to be informed of the increased likelihood of them making an error (thereby providing the surgeon with the most information possible when making a decision regarding treatment of the critical patient).

The example of FIG. 2 thus illustrates how different acceptable error likelihoods may be defined and how different types of intervention procedures may be implemented depending on the type of surgery, the current stage of surgery, the potential error event(s) associated with the type of surgery or current stage of surgery and the status (e.g. critical or non-critical) of the patient. It will be appreciated that FIG. 2 is, for the sake of clarity of explanation, a very simple example and that, in reality, the database stored in storage medium 108 may relate a large number of surgery types (not just the single surgery type "heart transplant"), surgery stages, potential error events, acceptable error likelihoods and intervention types. However, the principle of operation remains as described (the difference is that it occurs on a larger data set).

The information in the database may be preconfigured by a manufacturer of the surgical support system 100 with the most appropriate value of each acceptable error likelihood and the most appropriate intervention procedure for each surgery type or surgery stage being determined by the manufacturer. In particular, each acceptable error likelihood value may be determined by the manufacturer in advance by assessing, for each potential error event, the potential consequences of an error against the potential consequences of intervening in less serious errors. This information may be determined by reviewing historical surgical data, for example. Alternatively, or in addition, a surgeon may be able to customise the value of the acceptable error likelihood and the most appropriate intervention procedure for each surgery type or surgery stage depending on their personal preferences (e.g. using the user interface 115 to access and edit the database stored in storage medium 108).

As previously mentioned, in an example, the surgeon may select the type of surgical procedure (e.g. "heart transplant") which is to take place prior to the start of the surgical procedure using a suitable GUI menu system or the like. During the surgical procedure, the data processing apparatus 104 may be configured to detect the current stage (e.g. "Stage 1", "Stage 2" or "Stage 3") of the surgical procedure (enabling it to look up the appropriate potential error event(s) and associated acceptable error likelihood(s) and intervention type(s) for that stage) in one or more various ways.

In one example, a user (e.g. the surgeon or another member of the surgical team) may manually update the system each time the procedure moves on to a new stage. This may be done, for example, via the user interface 115 (e.g. by selecting the current stage from a list of the stages of the current procedure shown on a GUI menu system or the like) or via the audio monitoring system 114 (e.g. by saying a predetermined command, such as one or more words which uniquely identify the desired stage of the procedure, which is picked up by the audio monitoring system 113 and which is recognisable by the data processing device 104).

In another example, the data processing device 104 is configured to automatically detect the current stage of the procedure. In one example, this is done using a suitable machine vision image comparison technique (such methods are known in the art and will therefore not be discussed in detail here). At regular intervals during the procedure, an image is captured by the external and/or internal camera system 110, 111 and one or more characteristics of the captured image are compared with a corresponding one or more characteristics of each of images of a previous instance of the surgical procedure. Each image of a previous instance of the surgical procedure is an image known to have been captured at a particular stage of that previous instance of the surgical procedure. The particular stage of an image of a previous instance of the surgical procedure with the closest match with the captured image is determined to be the current stage of the procedure. In an example, the one or more characteristics of the captured image and each of the images of a previous instance of the procedure which are compared are determined using a machine learning classification technique. That is, each image of a previous instance of the procedure is manually classified as belonging to a particular stage of the procedure and a machine learning algorithm automatically determines one or more characteristics which distinguish that image from images belonging to other stages of the procedure. Those one or more characteristics are then analysed in a newly captured image (for which the classification is unknown) in order to determine the likely classification of that newly captured image.

Thus, for example, for the heart transplant surgical procedure of FIG. 2, at least one image for each of Stage 1, Stage 2 and Stage 3 will have been captured and manually classified as "Stage 1", "Stage 2" or "Stage 3" by a human user for one or more previous instances of a heart transplant procedure. The machine learning algorithm will have automatically determined one or more characteristics of each of these images which are indicative of the particular stage with which that image is associated. That is, the machine learning algorithm, given the images and manually applied classifications, will automatically determine one or more characteristics which distinguish a "Stage 1" image from a "Stage 2" or "Stage 3" image, one or more characteristics which distinguish a "Stage 2" image from a "Stage 1" or "Stage 3" image and one or more characteristics which distinguish a "Stage 3" image from a "Stage 1" or "Stage 2" image. During the procedure of FIG. 2, each image captured by the external or internal camera system 110, 111 is analysed in order to determine, based on the one or more characteristics of the previously captured "Stage 1", "Stage 2" and "Stage 3" images, whether or not the image is most likely to be "Stage 1", "Stage 2" or "Stage 3". The stage with which the image is most likely to be associated is then determined to be the current stage of the procedure.

Various machine learning algorithms are known in the art and will therefore not be discussed in detail here. It will be appreciated that the greater the number of images of the various stages of previous instances of the procedure and the greater the number of previous instances of the procedure from which those images are generated, the more reliable the determination of the current stage of the current procedure. Previous images may also be captured, for example, from different angles and/or under different lighting conditions in order to help provide more reliable determination of the current stage of the procedure (since the angle of view and/or lighting conditions for captured images of the current procedure are likely to vary for different instances of the procedure). Data indicative of the one or more characteristics of images of previous instances of the procedure for analysis of newly captured images of the current procedure is stored in the storage medium 108, for example.

In an embodiment, the automatic determination of the current stage of the surgical procedure may be confirmed manually by the surgeon (or another member of the surgical team) during the procedure. This helps to alleviate the risk of surgical errors taking place due to an erroneous determination of the current stage of the procedure (e.g. erroneous determination of "Stage 3" when it is actually "Stage 2"

being carried out, meaning that incorrect potential error events, acceptable error likelihoods and/or intervention procedures could be applied). In one example, this manual confirmation comprises inputting a confirmation command via the user interface 115 and/or audio monitoring system 112. For example, the user interface 115 displays the message "Automatic procedure stage detection=X-press OK or say CONFIRM to confirm" (wherein X is the name of the stage, e.g. "Stage 1", "Stage 2" or "Stage 3" for the example procedure of FIG. 2). If the user presses "OK" (e.g. "OK" being a virtual button displayed on a touch screen of the user interface 115) or vocally says "Confirm" (this being picked up by the audio monitoring system 113), then the data processing apparatus 104 knows that it has correctly determined the current surgical stage. On the other hand, if the user does not carry out this confirmation action within a predetermined time limit (e.g. 5 or 10 seconds), then the data processing apparatus 104 docs not rely on the automatically determined current stage of the procedure and, instead, awaits further input from the user in order for the current stage of the procedure to be manually selected.

The concept of automatically determining the current stage of the procedure based on a comparison between one of more characteristics of a newly captured image of the current procedure and one or more corresponding characteristics of one or more images of a previous instance of the procedure may be applied to the other types of surgical data which can be collected during the current and previous instances of the surgical procedure. For example, this may be applied to (i) surgical data generated by the surgical robot (e.g. from the movement of arms the actuators of joints), (ii) surgical data generated by the patient monitoring system, (iii) audio data collected by the audio monitoring system 113 during the current and previous instances of the surgical procedure (including verbal communication between members of the surgical team, audible machine alarms and the like) and/or (iv) surgical data generated by the surgeon monitoring system 114. Also, control data of an insufflator (not shown) or energy device may also be used for identifying the current stage of the surgical procedure, for example.

Different types of surgical data may be used to independently confirm the occurrence of particular events during the surgical procedure which are indicative of a particular stage of the surgical procedure taking place. In one example, the tools used by the surgeon at any given time during the procedure may be detected using both image recognition in images captured by the external and/or internal camera systems 110, 110 and monitoring devices on the tools (e.g. accelerometers forming part of the surgeon monitoring system 114) which output a signal as surgical data to the communication interface 107 when the tool concerned is picked up as opposed to being stationary on a surface. The use of a particular combination of tools may be mapped (in a database stored in storage medium 108, for example) to a particular stage of the procedure, thereby allowing the occurrence of that stage to be detected.

In an embodiment, the actions and/or body language of the surgeon (as detected using image recognition in images captured by the external and/or internal camera systems 110, 111 and/or by the surgeon monitoring system 114 comprising monitoring devices on the surgeon (e.g. accelerometers) which output a signal as surgical data indicating the movements of the surgeon) may also be used, in addition to the eye behaviour data, to help determine the likelihood of a surgeon making an error. For example, if the surgical data output by the monitoring devices indicates that the surgeon has deviated from an expected action (as indicated by the tools used by the surgeon) or from certain body language associated with safe surgical practice, then a suitable scaling factor (which is larger for larger deviations from safe surgical practice and smaller for smaller deviations from safe surgical practice, for example) is applied to the determined error likelihood to take this into account).

In an embodiment, the data processing apparatus 104 is operable to compare the obtained eye behaviour data of the surgeon and predetermined eye behaviour data associated with a predetermined likelihood of a surgeon making an error in the surgical procedure. The data processing apparatus 104 is operable to determine the likelihood of the surgeon making an error in the surgical procedure using the predetermined likelihood associated with the predetermined eye behaviour data and a result of the comparison between the obtained eye behaviour data of the surgeon and the predetermined eye behaviour data.

In an example, the value of each of a number of eye behaviour parameters are monitored. For example, one or more of the eye behaviour parameters of the dwell time on a region on interest, the fixation frequency on a region of interest, the velocity and/or distance of saccades, whether or not a region of interest has been overlooked and the pupil dilation of the surgeon is monitored. In an example, the region of interest is a portion of the surgeon's field of view of a predetermined size and shape and at a predetermined location in the surgeon's field of view. In another example, the region of interest is detected based on a suitable image recognition technique.

The value of each of the eye behaviour parameters (comprised within the eye behaviour data collected by the eye behaviour monitoring apparatus 101) is compared with one or more predetermined values of that eye behaviour parameter in order to determine an error likelihood associated with that parameter (parameter error likelihood). The predetermined eye behaviour parameter values are threshold values, for example, and the parameter error likelihood associated with a particular eye behaviour parameter depends on the relationship between the monitored value of that eye behaviour parameter and the one or more threshold values of that eye behaviour parameter.

In one example, an eye behaviour parameter has a single threshold value. For example, there may be a single threshold value of the dwell time on a particular region of interest (e.g. 0.5 seconds). If the monitored dwell time on the region of interest is less than the threshold value (e.g. less than 0.5 seconds), then the parameter error likelihood is set as 1. On the other hand, if the monitored dwell time on the region of interest is greater than the threshold value (e.g. greater than 0.5 seconds), then the parameter error likelihood set as 0.

In another example, an eye behaviour parameter has a plurality of threshold values. This allows a greater number of parameter error likelihoods to be defined and the parameter error likelihood depends on the position of the monitored parameter value with respect to the plurality of threshold values. For example, the dwell time on a particular region of interest may have three threshold values of successively increasing size (e.g. 0.25 seconds, 0.5 seconds and 0.75 seconds) monitored parameter values. If the monitored dwell time is less than the first (lowest) threshold value (e.g. less than 0.25 seconds), than the parameter error likelihood is determined to be the highest possible value (e.g. 1). If the monitored dwell time is between the first threshold and second (next lowest) threshold (e.g. between 0.25 and 0.5 seconds), then the parameter error likelihood is determined to be a lower value (e.g. 0.75). If the monitored parameter value is between the second threshold and the third (highest) threshold (e.g. between 0.5 and 0.75 seconds), then the parameter error likelihood is determined to be a lower value still (e.g. 0.25). If the monitored parameter value is greater than the third threshold (e.g. greater than 0.75 seconds), then the parameter error likelihood is determined to be the lowest possible value (e.g. 0).

It will be appreciated that, although the use of thresholds has been exemplified for the "dwell time on a region of interest" eye behaviour parameter, the use of thresholds may also be applied to any other eye behaviour parameter which takes the form of a numerical value related to the likelihood of the surgeon making an error (e.g. fixation frequency on a region of interest, saccade position and/or velocity and pupil dilation). The particular threshold value(s) for each monitored eye behaviour parameter and the parameter error likelihoods defined with respect to the threshold value(s) are chosen in advance for each potential error event associated with each surgery type and/or stage based on, for example, historical eye behaviour data of surgeons recorded during previous surgical procedures and data indicative of errors which occurred during those previous surgical procedures (including the surgical type and/or stage during which each error occurred). A suitable machine learning algorithm may be applied to this data set in order to determine the threshold value(s) and associated parameter error likelihoods, for example. In an example, the parameter error likelihood of the parameter of whether or not a region of interest has been overlooked will either be 0 (in case that the region of interest has not been overlooked) or 1 (in the case that the region of interest has been overlooked).

For a given potential error event (defined for a particular surgery type and/or stage), the parameter error likelihoods of each of the monitored eye behaviour parameters are combined in an appropriate manner to obtain the overall determined error likelihood (which is compared with the acceptable error likelihood for that potential error event). In one example, the determined error likelihood is a weighted sum of the parameter error likelihoods determined for each for the monitored eye behaviour parameters. For example, if five eye behaviour parameters are monitored (e.g. the dwell time on a region of interest, fixation frequency on a region of interest, the velocity and/or distance of saccades, whether or not a region of interest has been overlooked and the surgeon's pupil dilation), then the parameter error likelihoods determined for each of these parameters are added up with appropriate weightings to obtain the overall determined error likelihood value. In an example, each parameter error likelihood is determined to be between 0 and 1 (with 0 indicating the lowest possible error likelihood and 1 indicating the highest possible error likelihood). The weightings are chosen so that the overall determined error likelihood is also between 0 and 1. For example, if five monitored parameters are weighted equally, then the weightings of each would be 0.2 so as to ensure that the overall determined error likelihood is between 0 and 1. In another example, if a particular two of the monitored parameters are more indicative of an error occurring than the other three monitored parameters (e.g. based on the historical eye behaviour data), then the weightings of the particular two monitored parameters may be given higher weightings than the weightings of the other three monitored parameters (e.g. a weighing of 0.35 for each of the two more indicative parameters and a weighting of 0.1 for each of the three other parameters). The weightings may be adjusted for each eye behaviour parameter depending on the relevance of that eye behaviour parameter for the potential error event concerned (again based on the historical eye behaviour data, for example).

Thus, in embodiments, for each eye behaviour parameter monitored for a particular potential error event, the parameter error likelihood is determined based on the monitored value of the parameter and (if applicable) one or more threshold values which the monitored parameter value is compared. The overall determined error likelihood is then determined by combining the parameter error likelihoods of all monitored parameters (e.g. as a weighted sum). The overall determined error likelihood is then compared with the acceptable error likelihood defined for the potential error event in order to determine whether or not an intervention procedure should take place.

In one embodiment, eye behaviour parameters related to pupil behaviour (e.g. the parameters of pupil dilation and saccade velocity and/or distance) may be monitored in order to determine a general level of concentration, fatigue, etc. of the surgeon. Such eye behaviour parameters may be referred to as "concentration" or "fatigue" parameters. In another embodiment, eye behaviour parameters related to eye tracking (e.g. the parameters of dwell time on a region on interest, the fixation frequency on a region of interest, and whether or not a region of interest has been overlooked) may be monitored in order to determine an experience or skill level of the surgeon. Such eye behaviour parameters may be referred to as "experience" or "skill level" parameters.

For each potential error event (defined for each surgery type and/or stage, as exemplified in FIG. 2), the particular eye behaviour parameter(s) which are monitored, any parameter threshold value(s), the parameter error likelihoods associated with the parameter threshold value(s) and the weightings applied to the parameter error likelihoods when calculating the overall determined error likelihood are determined in advance. This allows the determined error likelihood for each potential error event to be calculated in the most appropriate way. This information for each potential error event is determined in advance of the surgery and stored as part of a database in the storage medium 108 (along with the acceptable error likelihood and intervention procedures for that potential error event).

As previously mentioned, the particular eye behaviour parameter(s) which are monitored, any parameter threshold value(s), the parameter error likelihoods associated with the parameter threshold value(s) and the weightings may be determined, for example, by collecting this information from previous instances of the surgical procedure with a known outcome. A suitable machine learning algorithm may be used, for example, on data of eye behaviour parameter values measured during previous instances of the surgical procedure and data indicating a measure of success (e.g. based on patient medical records) of those previous instances of the surgical procedure. Such data may be referred to generally as historical data.

This allows the machine learning algorithm to learn the most relevant eye behaviour parameters for each potential error event of each surgical procedure type and/or stage, thus allowing the eye behaviour parameters to be monitored for that potential error event to be determined and allowing the relative weightings of each eye behaviour parameter for calculating the overall determined error likelihood to be determined. It also allows (where relevant) the values of those eye behaviour parameters for which the likelihood of the potential error event occurring is increased (or decreased) by a certain amount to be determined, thereby allowing threshold(s) and parameter error likelihood(s) associated those threshold(s) to be defined.

For example, it may have been determined, based on previous instances of a heart transplant procedure, that the occurrence of the potential error event "lung damage" is correlated strongly with a dwell time on the patient's lung of less than 0.5 seconds and a pupil dilation of more than 50%. At the same time, the other eye behaviour parameters (such as fixation frequency on the lung) are found to be less strongly correlated with the occurrence of the potential error event "lung damage". In this case, the eye behaviour parameters of dwell time on the lung and pupil dilation are more highly weighted then the other eye behaviour parameters (such as fixation frequency on the lung) when determining the overall determined error likelihood or the potential error event. Furthermore, it is determined that a dwell time threshold of 0.5 seconds is appropriate and that a pupil dilation threshold 50% is most appropriate. The parameter error likelihood for each of these parameters is therefore determined during the current heart transplant procedure by comparing the dwell time and pupil dilation values monitored during the current heart transplant procedure with the threshold values 0.5 seconds and 50%, respectively.

Historical data may also be used to determine the parameter error likelihoods for a given parameter when the monitored value of that parameter is compared with the relevant threshold value. For example, the historical data may show that, for a dwell time on the lung of less than 0.5 seconds, the likelihood of an error occurring is 0.5 whereas for a dwell time of more than 0.5 seconds, likelihood of the error occurring is 0.15. These values are therefore associated with the determined threshold value 0.5 seconds. Thus, in the current heart transplant procedure, if the monitored dwell time on the lung is less than 0.5 seconds, then the parameter error likelihood for the potential error event "lung damage" is determined to be 0.5. On the other hand, if the monitored dwell time on the lung is greater than 0.5 seconds, then the parameter error likelihood for the potential error event "lung damage" is determined to be 0.15. This determined parameter error likelihood is then combined with the determined parameter error likelihood of each of the other monitored eye behaviour parameters (e.g. via a weighted sum) and compared with the acceptable error likelihood for the potential error event "lung damage". In the example of FIG. 2, an intervention procedure will take place if the determined error likelihood exceeds the acceptable error likelihood of 0.25.

For each potential error event, a region of interest (with respect to which the values of eye behaviour parameters such as dwell time and fixation frequency are calculated) is determined in advance so that it can be detected if the surgeon's gaze (that is, the location in space at which the surgeon is looking) is on the region of interest. The region(s) of interest may be different for different potential error events. For example, for the potential error event "lung damage", the region of interest is the lung of the patient. On the other hand, for the potential error event "artery damage", the region of interest is the artery of the patient.

Objects within the surgeon's field of view are mapped to corresponding positions within the surgeon's field of view in advance so as to enable the object at which the surgeon is looking at a given time to be determined. For example, if the surgeon is viewing a live video image of the patient (e.g. the image being captured by the external or internal camera systems 110, 111, transmitted to the communication interface 107 and then transmitted from the communication interface 107 to be displayed on a screen of the user interface 115), the field of view of the live video image is determined to be the surgeon's field of view and the region of the screen on which the video is displayed at which the surgeon is looking is determined to be the gaze position of the surgeon. A suitable image recognition technique (as known in the art) is used by the data processing apparatus 104 to detect relevant objects in the image (including any region(s) of interest) and the position on the screen of each object. The surgeon is determined to be looking at the detected object when the gaze position of the surgeon on the screen (as determined by the eye behaviour monitoring apparatus 101) overlaps with the position of a detected object on the screen.

Objects within the surgeon's field of view (in particular, region(s) of interest, e.g. a lung or artery of the patient) are recognisable by the data processing apparatus 104 based on, for example, a previously completed machine learning process in which images (e.g. of a lung, artery and the like) are classified using a suitable machine learning algorithm. Objects in newly captured images of a patient may thus be detected based on the previous machine learned classifications. Once the objects have been detected, it is determined (using the eye behaviour data) when the position of the surgeon's gaze overlaps the position of a detected object. When there is such an overlap, it is determined that the surgeon is looking at the detected object. When there is not such an overlap, it is determined that the surgeon is not looking at the detected object. In this way, eye behaviour parameters such as dwell time and fixation frequency on a detected object (e.g. a region of interest) can be determined.

In an embodiment, eye behaviour monitoring apparatus 101 and user interface 115 can be combined. For example, a user interface 115 may comprise a display (e.g. in the form of a touch screen or HMD) on which images of the surgical procedure (captured by the external or internal camera systems 110, 111) are displayed. The eye behaviour monitoring apparatus 101 (which comprises a further camera for capturing video images of the eyes of the surgeon so as to obtain the eye tracking and pupil monitoring data) is mounted in an appropriate position with respect to the display in order to monitor the surgeon's eyes as they view the displayed images.

Figure 3:
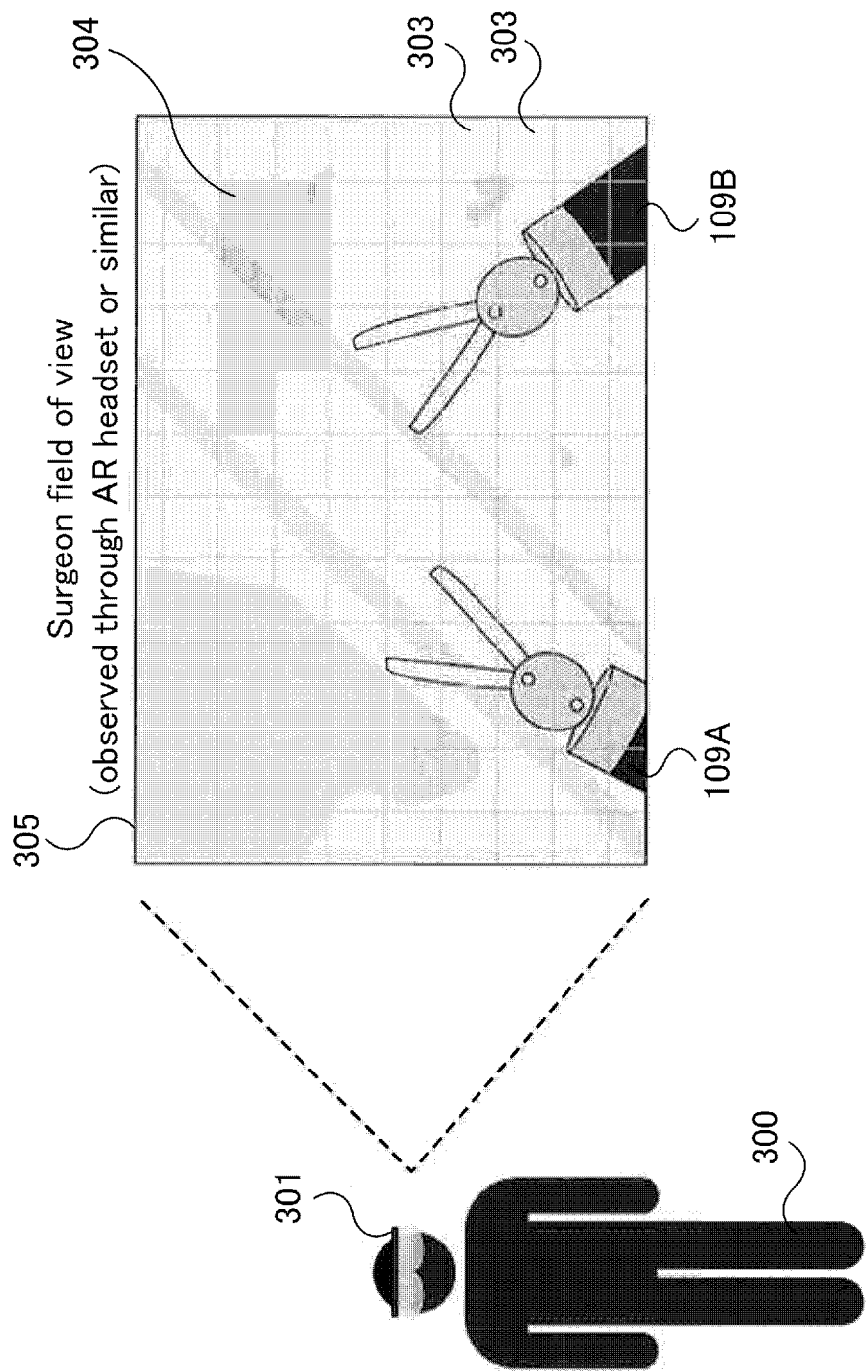
FIG. 3 schematically shows a first example implementation of the present technique.

FIG. 3 shows an example embodiment in which the surgeon 300 is wearing an HMD device 301. The surgeon wears the HMD device 301 as they perform the surgery to view images of inside the patient (as captured by the internal camera system 111) as they control arms 109A and 109B of the surgical robot 109 to perform the surgical procedure on a patient. An image 305 displayed to the surgeon by the HMD device 301 is shown. As well as the HMD device 301 comprising a display to display the image 305, the HMD device 301 also comprises the eye behaviour monitoring apparatus 101. This allows the position of the displayed image at which the surgeon is looking at any given time to be determined.

Image 305 is divided into a plurality of portions 303. Each portion 303 represents a portion of the image 305 at which the surgeon may be recorded as looking. In this example, a region 304 has been detected. The region 304 is made up of a plurality of image portions 303 for which it has been detected that the eye movements of the surgeon relative to these portions indicate that the determined error likelihood for a potential error event has exceeded the acceptable error likelihood. An intervention procedure is therefore initiated in which the region 304 is highlighted (e.g. as an AR overlay) in the image 305. This alerts the surgeon that their eye movements indicate that the risk of an error occurring in the region of the patient's body appearing within the region 304 is unacceptably high. This intervention procedure may be accompanied by one or more other intervention procedures (such as an audible alarm of haptic feedback, as previously described).

Highlighting of the region 304 occurs, for example, if the surgeon's dwell time on that region is unacceptably low or if the fixation frequency on that region is unacceptably low. In an example, the region 304 is associated with a potential error event and therefore the acceptable error likelihood with respect to which the determined error likelihood is compared is the acceptable error likelihood of that potential error event. The region 304 may be associated with a potential error event if it contains a region of interest associated with that potential error event. For example, if the procedure is Stage 1 of a heart transplant and a lung of the patient (as a region of interest) is detected within region 304, then it is determined that the potential error event associated with the region 304 is "lung damage". If, based on the surgeon's eye behaviour data, the determined error likelihood exceeds the acceptable error likelihood for "lung damage" (e.g. 0.25, according to FIG. 2), then the intervention procedures associated with "lung damage" are initiated. On the other hand, if an artery of the patient is contained in the region 304, then it is determined that the potential error event associated with the region 304 is "artery damage". If, based on the surgeon's eye behaviour data, the determined error likelihood exceeds the acceptable error likelihood for "artery damage" (e.g. 0.25, according to FIG. 2), then the intervention procedures associated with "artery damage" are initiated.

Figure 4A:
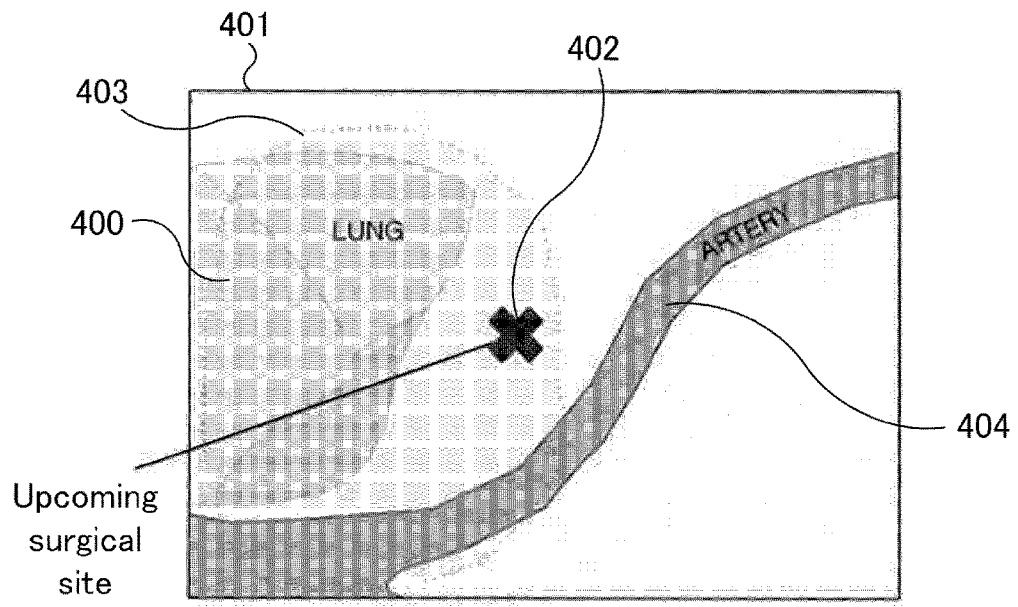
FIG. 4A schematically shows a second example implementation of the present technique.
Figure 4B:
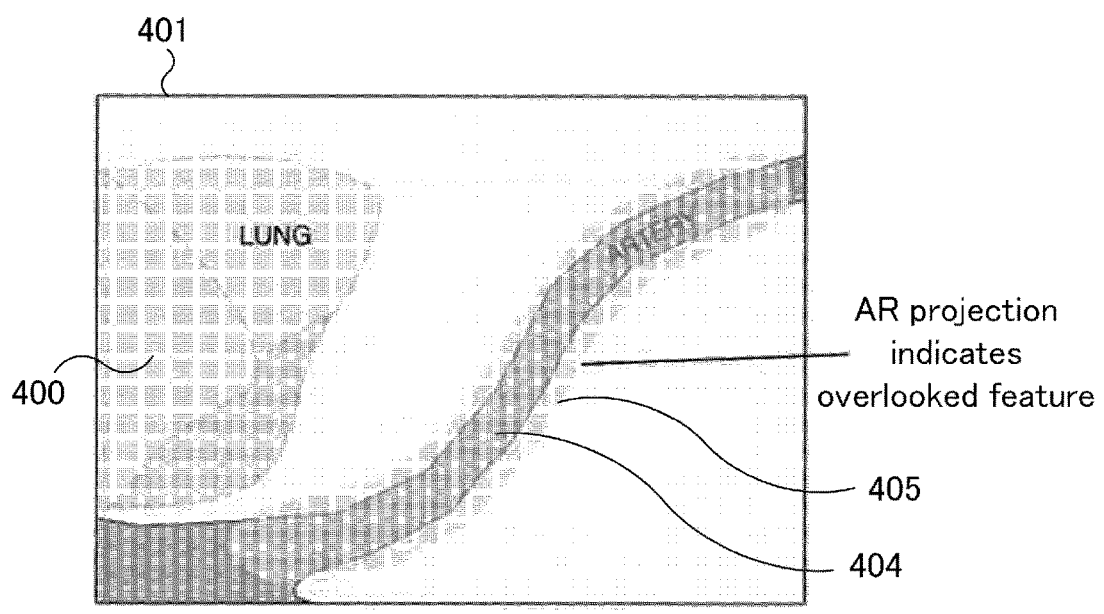
FIG. 4B schematically shows a second example implementation of the present technique.

FIGS. 4A and 4B show a more detailed demonstration of an example intervention procedure during stage 1 of the heart transplant. For the sake of clarity of explanation, only the single eye behaviour parameter of dwell time of the surgeon is considered and is used to determine the error likelihood for each potential error event (in this case, "lung damage" and "artery damage"). However, it will be appreciated that, in reality, a plurality of different eye behaviour parameters are simultaneously monitored and used to determine the error likelihood for each potential error event.

In this case, the surgeon plans to make an incision at location 402 situated between a lung 400 and an artery 404 of the patient. The surgeon is viewing the procedure via a display of the user interface 115 which displays an image 401 of the lung 400, artery 404 and incision location 402. The surgeon's eyes are being tracked in order to determine the dwell time of the surgeon on different areas of the image 401 (e.g. on each of portions into which the image 401 is divided up, like portions 303 in FIG. 3). Region 403 indicates an area with an acceptable dwell time (e.g. the dwell time is above the predetermined dwell time threshold). The region 403 includes the lung 400 but not the artery 404. The determined error likelihood is therefore below the acceptable error likelihood for the potential error event "lung damage". However, the determined error likelihood is above the acceptable error likelihood for the potential error event "artery damage". In this case, for case of explanation, it is assumed that the predetermined dwell time threshold for each of the potential error events "lung damage" and "artery damage" is the same.

In response to this, an intervention procedure is carried out. In this case, the intervention procedure comprises relaying an augmented reality projection 405 over the artery 404 in order to alert the surgeon that the likelihood of them damaging the artery 404 is unacceptably high. This is shown in FIG. 4B. The surgeon is therefore made aware of the potential error before it happens and is able to adjust their practice so as to ensure that they provide sufficient dwell time to the artery as well as the lung, therefore addressing the potential error and reducing the likelihood of it occurring.

Figure 5A:
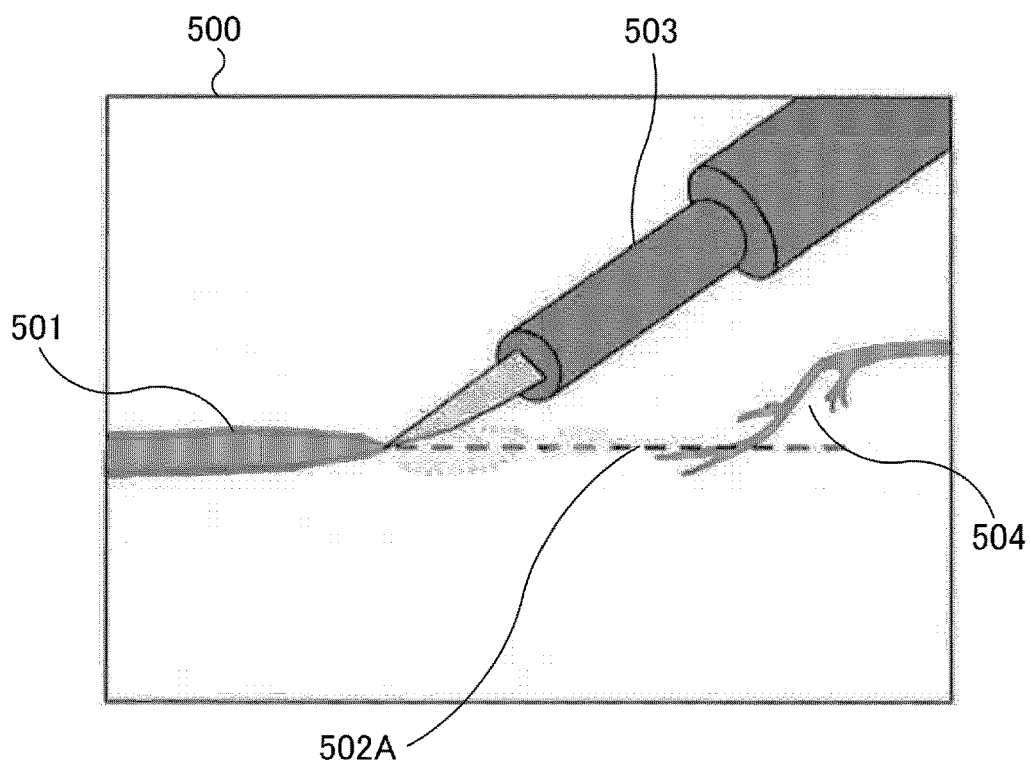
FIG. 5A schematically shows a third example implementation of the present technique.
Figure 5B:
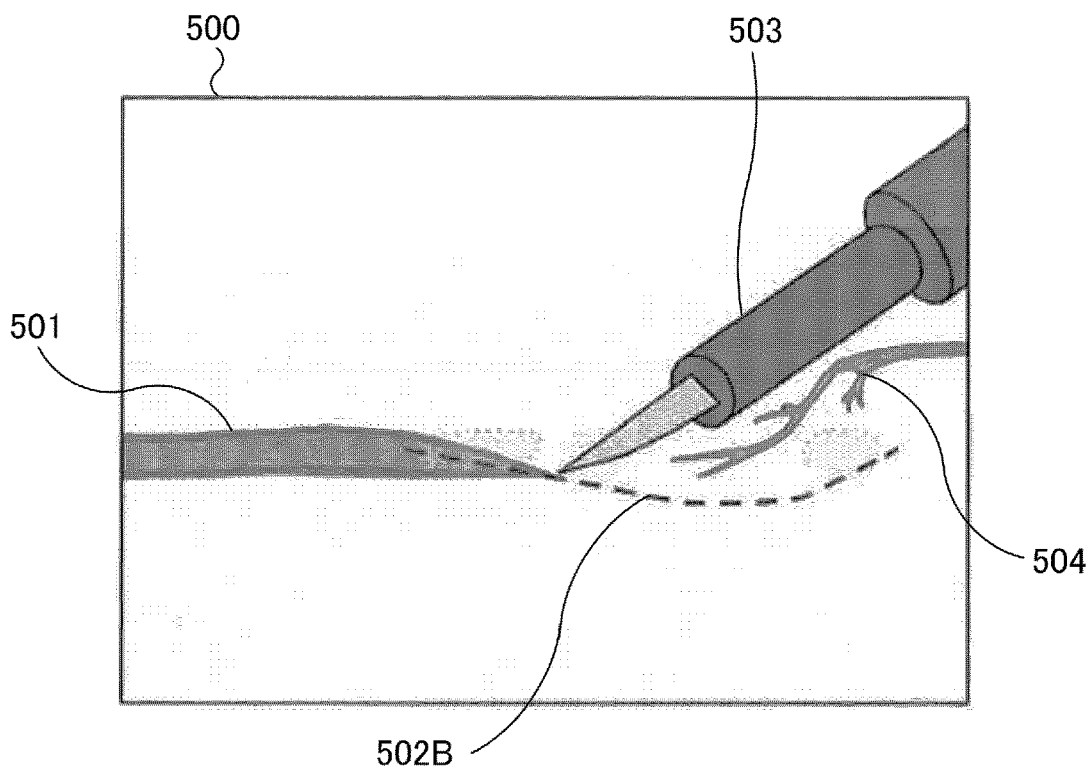
FIG. 5B schematically shows a third example implementation of the present technique.

FIGS. 5A and 5B show an example of stage 3 of the "heart transplant" procedure in which subsurface blood vessel damage is avoided by an intervention procedure involving automatic adjustment of the incision path. In this case, the surgeon is making an incision 501 along a pre-planned a predicted incision path 502A). The surgeon views the surgical site via a displayed image 500. The surgeon does this using a scalpel 503 which is held by the surgical robot 109. The surgeon controls the robot to move the scalpel 503 in order to make the incision. It has been detected that the predicted path 502A includes the sub-surface blood vessel 504. The scalpel is sufficiently close to the sub-surface blood vessel (i.e. less than a predetermined distance) that the data processing apparatus 104 determines that the surgeon may not have noticed the sub-surface blood vessel and that the sub-surface blood vessel may therefore by accidently severed. In response to this, as shown in FIG. 5B, the predicted incision path 502A is automatically adjusted to provide a new incision path 502B which avoids the sub-surface blood vessel 504. The intervention of adjusting the predicted path may be accompanied by other interventions (e.g. AR error visualisation and haptic alarm, as specified in FIG. 2) depending on, for example, the extend to which the predicted incision path 502A is adjusted so as to arrive at the new incision path 502B and/or the preconfigured preferences of the surgeon.

It will be appreciated that the discussed intervention procedures are only examples and that other intervention procedures are envisaged. For example, as well as an AR projection identifying areas with an unacceptably high determined error likelihood, the AR projection may also provide additional information to the surgeon in order to help advise as to why the intervention procedure has been initiated and what can be done in order to reduce the determined error likelihood back to an acceptable level. For example, if an intervention procedure comprises displaying an AR projection, then as well as the AR projection indicating the part of the image associated with the potential error event, the AR projection may also indicate to the surgeon (e.g. using text or a predetermined colour coding scheme) why the AR projection has been shown. For example, if the AR projection is shown because of an insufficient dwell time, a message "insufficient dwell time" is provided as part of the AR projection. Alternatively, or in addition, if the AR projection is shown because of an insufficient fixation frequency, then a message "insufficient fixation frequency" is provided as part of the AR projection. Other interventions procedures include, for example alerting another human (e.g. another surgeon) or an AI (artificial intelligence) assistant from whom a surgeon may seek assistance or even passing control to another human (e.g. a more experienced surgeon) who takes over the surgical procedure until the stage for which the determined error likelihood was found to be unacceptably has been completed. Such a system may be useful in surgical training, for example.

In an embodiment, as well as providing an intervention procedure based on eye behaviour data of the surgeon, the surgeon's eye behaviour data can also be used to determine the current ability and/or confidence of the surgeon at the beginning the surgical procedure (e.g. using known relationships between eye behaviour of the surgeon and ability and/or confidence). The order in which the stages of the surgical procedure are carried out is then determined based on the surgeon's determined ability and/or confidence (for procedures in which this is possible).

For example, prior to the beginning of a procedure, a surgeon is shown images of various stages of a previous instance of the surgical procedure from various angles and the eye behaviour data the surgeon is collected whilst the surgeon views these images. In response to the analysis of this eye behaviour data, the data processor 104 determines areas of the surgical sight related likely to be related to a higher error likelihood. If possible (depending on the type of procedure), the surgeon is instructed to carry out the stages of the procedure involving regions associated with a lower error likelihood to be carried out first. This helps provide a successful start to the procedure. This helps establishes the surgeon's workflow and improves their confidence for the later and more difficult stages of the procedure (which are associated with a higher error likelihood). The data processing apparatus 104 determine the order of the stages of the procedure (for procedures for which this is possible) by, for example, determining the error likelihood of each of the stages based on the surgeon's eye behaviour data and ranking the stages in order of lowest error likelihood to highest error likelihood. The stages are then carried out in the order determined by this ranking (so that the stage associated with the lowest error likelihood occurs first followed by the stages with successfully higher error likelihoods).

In an embodiment, when the surgeon carries out the procedure by viewing an image displayed using a display of the user interface 115 and the determined error likelihood exceeds the acceptable error likelihood for a given potential error event, the data processing apparatus may control the user interface 115 to display a close up (that is, zoomed in) version of the region of the displayed image associated with the unacceptably high error likelihood (e.g. the portion of the image 401 comprising the artery 404 in FIGS. 4A and 4B or the portion or the portion of the image 500 comprising the sub-surface blood vessel 504 in FIGS. 5A and 5B). When this zoomed in image is displayed, eye behaviour data of the surgeon as they view the zoomed in image is collected. This enables a sub-region within the zoomed in image with which the unacceptably high error likelihood is associated to be determined.

This allows the specific cause of an unacceptably high error likelihood to be determined when the displayed field of view is sufficiently wide such that the unacceptably high error likelihood has a plurality of potential causes. For example, when the image 401 comprising both the lung 400 and the artery 401 is displayed, then it may be difficult to determine from certain eye behaviour parameters (e.g. high saccade distance and/or velocity) whether the determined error likelihood is associated with the lung or with the artery. By displaying successive zoomed in images of (a) the region of image 401 containing the lung 400 and (b) the region of image 401 containing the artery 404 and, for each successively displayed zoomed in image, performing further eye behaviour analysis of the surgeon as they view the zoomed in image, it is possible to narrow down the source of the uncertainly to either the lung 400 or the artery 404 (e.g. if the high saccade distance and/or velocity is maintained when the zoomed in image of the lung 400 is shown but not when the zoomed in image of the artery 404 is shown, it is determined that the unacceptably high error likelihood associated with the high saccade distance and/or velocity is related to the lung 400 rather than the artery 404). This enables a wider view of the surgical sight to be provided to the surgeon (so as to enable the surgeon simultaneously monitor a larger number of events) whilst, at the same time, allows the source of any unacceptably high error likelihood to be determined more accurately.

In an embodiment, when a region of a displayed image is associated with an unacceptably high error likelihood based on eye behaviour data of the surgeon, the image (or, at least, the region of the image with which the high error likelihood is associated) can be shown with a different visual characteristic (e.g. a different application of false colour, lines, shading or the like) in order to attempt to provide a clearer image to the surgeon (that is, an image for which it is easier for the surgeon to understand what is happening). A plurality of different predetermined visual characteristics (image effects) can be successively applied to the displayed image (or relevant image region) by the user interface 115 (as controlled by the data processing apparatus 104). After each image effect is applied, eye behaviour data of the surgeon is collected in order to determine whether the error likelihood has decreased with that applied effect. The successive display of different effects and of the collection of associated eye behaviour data is another example of an intervention procedure (in particular, it represents an adjustment of images displayed on the screen of the user interface 115 relied on by the surgeon to carry out the surgical procedure). This allows each of the predetermined effects to be successively applied to the image (or relevant image region) until the error likelihood is reduced to an acceptable level. If none of the effects result in the error likelihood being sufficiently reduced, then another intervention procedure may be initiated. The application of a plurality of different image effects to the image in order to make it easier for the surgeon to understand the image and to therefore reduce the error likelihood associated with the image allows an unacceptably high error likelihood to potentially be corrected prior to a more invasive intervention procedure (e.g. suspension of display of the image or suspension of operation of the surgical robot 109) being applied. This helps to alleviate disruption of the surgeon's workflow.

Figure 6:
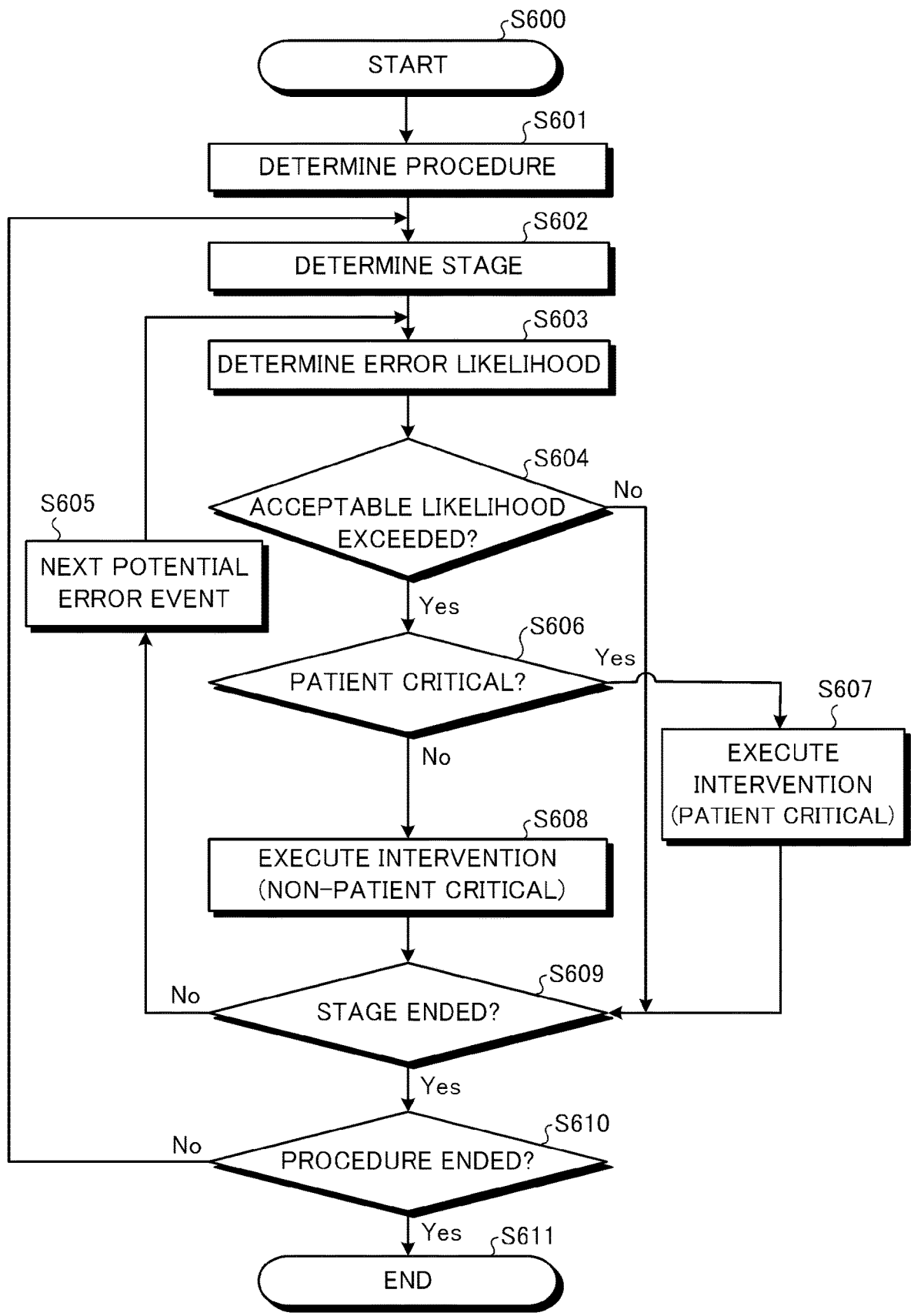
FIG. 6 shows a flow chart showing a first method, according to an embodiment.

FIG. 6 shows a method according to an embodiment of the present technique. The method starts at step 600. At step 601, the type of surgical procedure (e.g. heart transplant) is determined. This is selected manually by the surgeon using the user interface 115 prior to beginning the procedure, for example (as previously described). At step 602, during the procedure, the current stage of the procedure (e.g. stage 1, stage 2 or stage 3 of the heart transplant) is determined. This is carried out automatically by the data processing apparatus 104 based on image recognition, for example (as previously described). At step 603, the error likelihood of a first one of the potential error events associated with the determined stage of the surgical procedure (e.g. "lung damage" for stage 1 of the heart transplant) is determined. At step 604, it is determined whether or not the determined error likelihood of the potential error event exceeds the acceptable error likelihood for that potential error event.

If the determined error likelihood does not exceed the acceptable error likelihood at step 604, then the method proceeds to step 609, in which it is determined whether or not the current surgical stage has ended. If the current surgical stage has not ended, then the method proceeds to step 605, in which the next potential error event associated with the current stage of the surgical procedure (e.g. "artery damage" for stage 1 of the heart transplant) is selected. The method then returns to step 603, in which the error likelihood of the selected next potential error event is determined. If the current surgical stage has ended, then the method proceeds to step 610, in which it is determined whether or not the procedure has ended. If the procedure has not ended, then the method returns to step 602 so that the next surgical stage (e.g. stage 2 of the heart transplant if stage 1 has ended or stage 3 of the heart transplant if stage 2 has ended) is determined. The error likelihood of the first potential error event of the next surgical stage is then determined at step 603. If the procedure has ended, then the method ends at step 611.

If the determined error likelihood does exceed the acceptable error likelihood at step 604, then the method proceeds to step 606, in which it is determined whether or not the patient is in a critical condition. If the patient is in a critical condition, then the method proceeds to step 607, in which an intervention procedure preconfigured to take place when the patient is in a critical condition is executed. If the patient is determined not to be in a critical condition, then the method proceeds to step 608, in which an intervention procedure preconfigured to take place when the patient is not in a critical condition is executed. The procedure then proceeds to step 609.

Although the above-mentioned embodiments relate to determining the likelihood of a surgeon making an error based on obtained eye behaviour data, it will be appreciated that this principle may be extended to any parameter (intervention parameter) for which a value may be determined based on eye behaviour of the surgeon and on the basis of which an intervention procedure may be determined. For example, the intervention parameter may indicate a level of experience or a level of fatigue of the surgeon. In the case of the eye behaviour data indicating the level of experience of the surgeon, an intervention procedure may be implemented for a less experienced surgeon (e.g. a surgeon for which the determined intervention parameter indicative of the surgeon's experience is less than a predetermined threshold) but not for a more experienced surgeon (e.g. a surgeon for which the determined intervention parameter indicative of the surgeon's experience is greater than a predetermined threshold). Similarly, in the case of the eye behaviour data indicating the level of fatigue of the surgeon, an intervention procedure may be implemented for a more fatigued surgeon (e.g. a surgeon for which the determined intervention parameter indicative of the surgeon's fatigue is greater than a predetermined threshold) but not for a less fatigued surgeon (e.g. a surgeon for which the determined intervention parameter indicative of the surgeon's fatigue is less than a predetermined threshold). Parameters indicative of the error likelihood of the surgeon, the level of experience of the surgeon and/or the level of fatigue of the surgeon are all examples of intervention parameters.

Figure 7:
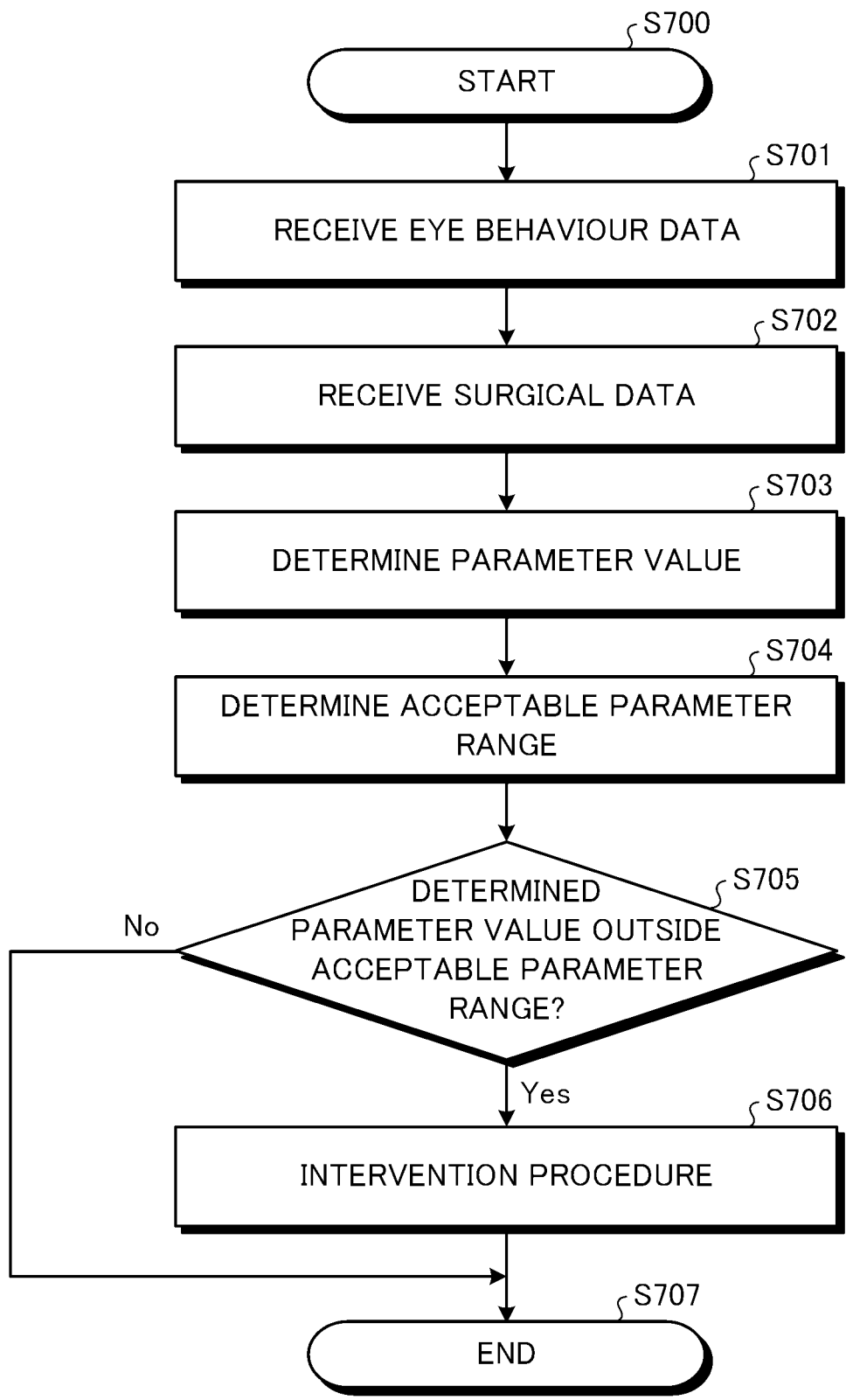
FIG. 7 shows a flow chart showing a second method, according to an embodiment.

FIG. 7 shows a flow chart showing a method implemented by the data processing apparatus 104, according to an embodiment. The method starts at step 700. At step 701, the communication interface 107 receives eye behaviour data from the eye behaviour monitoring apparatus 101. At step 702, the communication interface 107 receives surgical data generated by one or more of the surgical data generating apparatuses 109 to 115. At step 703, the processor 105 determines a value of an intervention parameter associated with the surgical procedure using the obtained eye behaviour data. At step 704, the processor 105 determines an acceptable range of the value of the intervention parameter using the generated surgical data. At step 705, it is determined whether or not the determined value of the intervention parameter is outside the determined acceptable range of the value of the intervention parameter. If no, then the method ends at step 707. If yes, then the method proceeds to step 706, in which the communication interface 107 outputs a signal to control a surgical intervention apparatus (e.g. user interface 115 or surgical robot 109) to perform an intervention procedure for intervening in the surgeon's performance of the surgical procedure. The method then ends at step 707.

In an embodiment, the surgical data (e.g. data from patient monitoring system 112) indicative of the condition of the patient (e.g. critical or non-critical) may be used to determine the acceptable error likelihood (or, more generally, the acceptable range of the intervention parameter) instead of or in addition to the intervention type for a given procedure type and stage. For example, the acceptable error likelihood may be higher for a critical patient (thereby allowing more autonomy for the surgeon) than for a non-critical patient. It will be appreciated that the surgical data indicative of the condition of the patient may be used in any suitable way in order to determine the type of intervention procedure and when that intervention procedure is to be implemented.

Some embodiments of the present technique are defined by the following numbered clauses:

(1)
A surgical support system including:
an eye behaviour monitoring apparatus operable to monitor eye behaviour of a surgeon performing a surgical procedure to obtain eye behaviour data of the surgeon;
a surgical data generating apparatus operable to generate surgical data associated with the surgical procedure being performed by the surgeon;
a surgical intervention apparatus operable to perform an intervention procedure for intervening in the surgeon's performance of the surgical procedure; and
a data processing apparatus operable to:
determine a value of an intervention parameter associated with the surgical procedure using the obtained eye behaviour data;
determine an acceptable range of the value of the intervention parameter using the generated surgical data, and
if the determined value of the intervention parameter is outside the determined acceptable range of the value of the intervention parameter, control the surgical intervention apparatus to perform the intervention procedure for intervening in the surgeon's performance of the surgical procedure.

(2)
A surgical support system according to clause (1), wherein the eye behaviour data is one of pupil monitoring data and eye tracking data.

(3)
A surgical support system according to clause (1) or (2), wherein the intervention parameter is indicative of a likelihood of the surgeon making an error in the surgical procedure and the acceptable range of the value of the intervention parameter is indicative of an acceptable likelihood of the surgeon making an error in the surgical procedure.

(4)
A surgical support system according to clause (3), wherein the data processing apparatus is operable:
to compare the obtained eye behaviour data of the surgeon with predetermined eye behaviour data associated with a predetermined likelihood of a surgeon making an error in the surgical procedure;
to determine the likelihood of the surgeon making an error in the surgical procedure using the predetermined likelihood associated with the predetermined eye behaviour data and a result of the comparison between the obtained eye behaviour data of the surgeon and the predetermined eye behaviour data.

(5)

A surgical support system according to clause (4), wherein the generated surgical data is indicative of at least one of a type of the surgical procedure, a current stage of the surgical procedure and a current condition of the patient of the surgical procedure.

(6)

A surgical support system according to clause (5), wherein the data processing apparatus is operable to select the predetermined eye behaviour data using the generated surgical data.

(7)

A surgical support system according to clause (5), wherein the intervention procedure is selected using the generated surgical data.

(8)

A surgical support system according to any one of clauses (3) to (7), wherein the intervention procedure includes outputting an alert signal indicating that the determined likelihood of the surgeon making an error in the surgical procedure exceeds the acceptable likelihood of the surgeon of the surgeon making an error in the surgical procedure.

(9)

A surgical support system according to clause (8), wherein the alert signal is a visual indication displayed on a display on which a surgical image is displayed.

(10)

A surgical support system according to clause (9), wherein the visual indication is superimposed in a vicinity of a region of interest in the surgical image.

(11)

A surgical support system according to any one of clauses (3) to (10), wherein the intervention procedure includes providing an adjustment signal to a surgical apparatus used by the surgeon to perform a surgical function in the surgical procedure to control the surgical apparatus to adjust the performed surgical function to pre-empt the error in the surgical procedure.

(12)

A surgical support system according to any one of clauses (3) to (11), wherein the data processing apparatus is operable:
  to determine, using the obtained eye behaviour data, a region of a field of view of the surgeon with which an error the likelihood of which has been determined is associated; and
  to determine the intervention procedure based on a characteristic of the determined region of the field of view of the surgeon.

(13)

A surgical support system according to clause (12), wherein the data processing apparatus is operable:
  to output, for display, an image representative of the region of the field of view of the surgeon for viewing by the surgeon;
  to control the eye behaviour monitoring apparatus to obtain further eye behaviour data of the surgeon as the surgeon views the displayed image; and
  to determine the intervention procedure using the further eye behaviour data of the surgeon.

(14)

A surgical support system according to clause (13), wherein the data processing apparatus is operable:
  to determine, using the obtained further eye behaviour data, a sub-region of the region of the field of view of the surgeon with which an error the likelihood of which has been determined is associated; and
  to determine the intervention procedure based on a characteristic of the determined sub-region of the region of the field of view of the surgeon.

(15)

A surgical support system according to any one of clauses (3) to (14), wherein the data processing apparatus is operable:
  to determine, using the obtained eye behaviour data, a region of a field of view of the surgeon with which an error the likelihood of which has been determined is associated;
  to output, for display, an image representative of the region of the field of view of the surgeon for viewing by the surgeon; and
  to control the eye behaviour apparatus to obtain further eye behaviour data of the surgeon as the surgeon views the displayed image;
  wherein the intervention procedure includes adjusting a display characteristic of the displayed image and determining, using the further eye behaviour data of the surgeon, an adjusted display characteristic which reduces the likelihood of the error associated with the region of the field of view of the surgeon.

(16)

A data processing apparatus for a surgical support system, the surgical support system including an eye behaviour monitoring apparatus operable to monitor eye behaviour of a surgeon performing a surgical procedure to obtain eye behaviour data of the surgeon, a surgical data generating apparatus operable to generate surgical data associated with the surgical procedure being performed by the surgeon and a surgical intervention apparatus operable to perform an intervention procedure for intervening in the surgeon's performance of the surgical procedure, wherein the data processing apparatus includes circuitry configured to:
  receive the obtained eye behaviour data;
  receive the generated surgical data;
  determine a value of an intervention parameter associated with the surgical procedure using the obtained eye behaviour data,
  determine an acceptable range of the value of the intervention parameter using the generated surgical data, and
  if the determined value of the intervention parameter is outside the determined acceptable range of the value of the intervention parameter, output a signal to control the surgical intervention apparatus to perform the intervention procedure for intervening in the surgeon's performance of the surgical procedure.

(17)

A method of operating a surgical support system, the surgical support system including an eye behaviour monitoring apparatus operable to monitor eye behaviour of a surgeon performing a surgical procedure to obtain eye behaviour data of the surgeon, a surgical data generating apparatus operable to generate surgical data associated with the surgical procedure being performed by the surgeon and a surgical intervention apparatus operable to perform an intervention procedure for intervening in the surgeon's performance of the surgical procedure, wherein the method includes:
  receiving the obtained eye behaviour data;
  receiving the generated surgical data;
  determining a value of an intervention parameter associated with the surgical procedure using the obtained eye behaviour data, determining an acceptable range of the value of the intervention parameter using the generated surgical data, and if the determined value of the intervention parameter is outside the determined acceptable range of the value of the intervention parameter, outputting a signal to control the surgical intervention apparatus to perform the intervention procedure for intervening in the surgeon's performance of the surgical procedure.

(18)

A program for controlling a computer to perform a method according to clause (17).

(19)

A storage medium storing a program according to clause (18).

Numerous modifications and variations of the present disclosure are possible in light of the above teachings. It is therefore to be understood that within the scope of the appended claims, the disclosure may be practiced otherwise than as specifically described herein.

In so far as embodiments of the disclosure have been described as being implemented, at least in part, by software-controlled data processing apparatus, it will be appreciated that a non-transitory machine-readable medium carrying such software, such as an optical disk, a magnetic disk, semiconductor memory or the like, is also considered to represent an embodiment of the present disclosure.

It will be appreciated that the above description for clarity has described embodiments with reference to different functional units, circuitry and/or processors. However, it will be apparent that any suitable distribution of functionality between different functional units, circuitry and/or processors may be used without detracting from the embodiments.

Described embodiments may be implemented in any suitable form including hardware, software, firmware or any combination of these. Described embodiments may optionally be implemented at least partly as computer software running on one or more data processors and/or digital signal processors. The elements and components of any embodiment may be physically, functionally and logically implemented in any suitable way. Indeed the functionality may be implemented in a single unit, in a plurality of units or as part of other functional units. As such, the disclosed embodiments may be implemented in a single unit or may be physically and functionally distributed between different units, circuitry and/or processors.

Although the present disclosure has been described in connection with some embodiments, it is not intended to be limited to the specific form set forth herein. Additionally, although a feature may appear to be described in connection with particular embodiments, one skilled in the art would recognize that various features of the described embodiments may be combined in any manner suitable to implement the technique.

REFERENCES

NPL 1: Tien, T., Pucher, P. H., Sodergren, M. H. et al. Surg Endosc (2015) 29: 405. https://doi.org/10.1007/s00464-014-3683-7

NPL 2: Tim Stockdale "World's first study of rider's eye movements could reveal the key to show jumping success" http://www.timstockdale.com/worlds-first-study-of-riders-eye-movements-could-revea 1-the-key-to-show-jumping-success/

NPL 3: SUNY Downstate Medical Center. "Novice pilots improve visual responses to simulation by watching experts' eye movements: Eye movements reliably distinguish between novice and expert military pilots." ScienceDaily. ScienceDaily, 27 Nov. 2017. <www.sciencedaily.com/releases/2017/11/171127152038.htm>

The invention claimed is:

1. A surgical support system comprising:
   an eye monitor to monitor eye behaviour of a surgeon performing a surgical procedure to obtain eye behaviour data of the surgeon;
   a surgical data sensor to generate surgical data associated with the surgical procedure being performed by the surgeon;
   a surgical intervention circuit configured to perform an intervention procedure for intervening in the surgeon's performance of the surgical procedure; and
   a processing circuit configured to:
   determine a value of an intervention parameter associated with the surgical procedure using the obtained eye behaviour data, wherein the intervention parameter is indicative of a likelihood of a potential error event in the surgical procedure based on eye behaviour data of the surgeon;
   determine an acceptable range of the value of the intervention parameter using the generated surgical data and the potential error event, wherein the acceptable range of the value of the intervention parameter being indicative of an acceptable likelihood of the surgeon making the potential error event, and
   if the determined value of the intervention parameter is outside the determined acceptable range of the value of the intervention parameter, control the surgical intervention circuit to perform the intervention procedure for intervening in the surgeon's performance of the surgical procedure, wherein the intervention procedure includes:
   outputting an alert signal indicating that the determined likelihood of the surgeon making the potential error event in the surgical procedure exceeds the acceptable likelihood; and/or
   providing an adjustment signal to a surgical apparatus used by the surgeon to perform a surgical function in the surgical procedure to control the surgical apparatus to adjust the performed surgical function to pre-empt the potential error event in the surgical procedure.

2. A surgical support system according to claim 1, wherein the eye behaviour data is one of pupil monitoring data and eye tracking data.

3. A surgical support system according to claim 1, wherein the processing circuit is configured to:
   to compare the obtained eye behaviour data of the surgeon with predetermined eye behaviour data associated with a predetermined likelihood of a surgeon making an error in the surgical procedure; and
   to determine the likelihood of the surgeon making an error in the surgical procedure using the predetermined likelihood associated with the predetermined eye behaviour data and a result of the comparison between the obtained eye behaviour data of the surgeon and the predetermined eye behaviour data.

4. A surgical support system according to claim 3, wherein the generated surgical data is indicative of at least one of a type of the surgical procedure, a current stage of the surgical procedure and a current condition of the patient of the surgical procedure.

5. A surgical support system according to claim 4, wherein the processing circuit is configured to select the predetermined eye behaviour data using the generated surgical data.

6. A surgical support system according to claim 4, wherein the processing circuit is configured to select an intervention procedure using the generated surgical data and the potential error event and control the surgical intervention circuit to perform the selected intervention procedure.

7. A surgical support system according to claim 1, wherein the alert signal is a visual indication displayed on a display on which a surgical image is displayed.

8. A surgical support system according to claim 7, wherein the visual indication is superimposed in a vicinity of a region of interest in the surgical image.

9. A surgical support system according to claim 1, wherein the processing circuit is configured:
  to determine, using the obtained eye behaviour data, a region of a field of view of the surgeon with which an error the likelihood of which has been determined is associated; and
  to determine the intervention procedure based on a characteristic of the determined region of the field of view of the surgeon and the potential error event.

10. A surgical support system according to claim 9, wherein the processing circuit is configured:
  to output, for display, an image representative of the region of the field of view of the surgeon for viewing by the surgeon;
  to control the eye behaviour monitoring apparatus to obtain further eye behaviour data of the surgeon as the surgeon views the displayed image; and
  to determine the intervention procedure using the further eye behaviour data of the surgeon.

11. A surgical support system according to claim 10, wherein the processing circuit is configured:
  to determine, using the obtained further eye behaviour data, a sub-region of the region of the field of view of the surgeon with which an error the likelihood of which has been determined is associated; and
  to determine the intervention procedure based on a characteristic of the determined sub-region of the region of the field of view of the surgeon.

12. A surgical support system according to claim 1, wherein the processing circuit is configured:
  to determine, using the obtained eye behaviour data, a region of a field of view of the surgeon with which an error the likelihood of which has been determined is associated;
  to output, for display, an image representative of the region of the field of view of the surgeon for viewing by the surgeon; and
  to control the eye monitor to obtain further eye behaviour data of the surgeon as the surgeon views the displayed image;
  wherein the intervention circuit is configured to adjust a display characteristic of the displayed image and determine, using the further eye behaviour data of the surgeon, an adjusted display characteristic which reduces the likelihood of the error associated with the region of the field of view of the surgeon.

13. A surgical support system according to claim 1, wherein the processing circuit is further configured to: determine a current condition from the generated surgical data; select an intervention procedure using the current condition of the patient of the surgical procedure; and output a signal to control the surgical intervention circuit to perform the selected intervention procedure.

14. A data processing apparatus for a surgical support system, the surgical support system comprising an eye monitor to monitor eye behaviour of a surgeon performing a surgical procedure to obtain eye behaviour data of the surgeon, a surgical data sensor to generate surgical data associated with the surgical procedure being performed by the surgeon and a surgical intervention circuit to perform an intervention procedure for intervening in the surgeon's performance of the surgical procedure, wherein the data processing apparatus comprises circuitry configured to:
  receive the obtained eye behaviour data;
  receive the generated surgical data;
  determine a value of an intervention parameter associated with the surgical procedure using the obtained eye behaviour data, wherein the intervention parameter is indicative of a likelihood of a potential error event in the surgical procedure based on eye behaviour data of the surgeon,
  determine an acceptable range of the value of the intervention parameter using the generated surgical data and the potential error event, wherein the acceptable range of the value of the intervention parameter being indicative of an acceptable likelihood of the surgeon making the potential error event, and
  if the determined value of the intervention parameter is outside the determined acceptable range of the value of the intervention parameter, output a signal to control the surgical intervention circuit to perform the intervention for intervening in the surgeon's performance of the surgical procedure,
  intervention circuit to perform the intervention procedure for intervening in the surgeon's performance of the surgical procedure, wherein the intervention procedure includes:
  outputting an alert signal indicating that the determined likelihood of the surgeon making the potential error event in the surgical procedure exceeds the acceptable likelihood; and/or
  providing an adjustment signal to a surgical apparatus used by the surgeon to perform a surgical function in the surgical procedure to control the surgical apparatus to adjust the performed surgical function to pre-empt the potential error event in the surgical procedure.

15. A data processing apparatus according to claim 14, wherein the generated surgical data is indicative of at least one of a type of the surgical procedure, a current stage of the surgical procedure and a current condition of the patient of the surgical procedure.

16. A method of operating a surgical support system, the surgical support system comprising an eye monitor configured to monitor eye behaviour of a surgeon performing a surgical procedure to obtain eye behaviour data of the surgeon, a surgical data sensor to generate surgical data associated with the surgical procedure being performed by the surgeon and a surgical intervention circuit configured to perform an intervention procedure for intervening in the surgeon's performance of the surgical procedure, wherein the method comprises:
  receiving the obtained eye behaviour data;
  receiving the generated surgical data;
  determining a value of an intervention parameter associated with the surgical procedure using the obtained eye behaviour data, wherein the intervention parameter is indicative of a likelihood of a potential error event in the surgical procedure based on eye behaviour data of the surgeon,
  determining an acceptable range of the value of the intervention parameter using the generated surgical data and the potential error event, wherein the acceptable range of the value of the intervention parameter being indicative of an acceptable likelihood of the surgeon making the potential error event, determining whether the value of the intervention parameter is within the acceptable range, and in response to the value of the intervention parameter being outside the acceptable range, outputting a signal to control the surgical intervention circuit to perform the intervention procedure for intervening in the surgeon's performance of the surgical procedure, wherein the intervention procedure includes:

outputting an alert signal indicating that the determined likelihood of the surgeon making the potential error event in the surgical procedure exceeds the acceptable likelihood; and/or providing an adjustment signal to a surgical apparatus used by the surgeon to perform a surgical function in the surgical procedure to control the surgical apparatus to adjust the performed surgical function to pre-empt the potential error event in the surgical procedure.

17. A non-transitory, computer readable storage medium storing a program for controlling a computer to perform a method according to claim 6.

18. A method according to claim 16, further comprising:
selecting an intervention procedure using the generated surgical data and the potential error event; and
outputting a signal to control the surgical intervention circuit to perform the selected intervention procedure.

19. A method according to claim 16, further comprising: determining a current condition from the generated surgical data; selecting an intervention procedure using the current condition of the patient of the surgical procedure; and outputting a signal to control the surgical intervention circuit to perform the selected intervention procedure.

20. A method according to claim 16, wherein the generated surgical data is indicative of at least one of a type of the surgical procedure, a current stage of the surgical procedure and a current condition of the patient of the surgical procedure.

* * * * *